US009439597B2

(12) United States Patent
Warrick et al.

(10) Patent No.: US 9,439,597 B2
(45) Date of Patent: Sep. 13, 2016

(54) METHOD AND APPARATUS FOR MONITORING A FETUS DURING LABOR

(71) Applicant: PERIGEN, INC., Princeton, NJ (US)

(72) Inventors: Philip A. Warrick, Montreal (CA); Emily Hamilton, Verdun (CA)

(73) Assignee: PERIGEN INC., Cranbury, NJ (US)

( * ) Notice: Subject to any disclaimer, the term of this patent is extended or adjusted under 35 U.S.C. 154(b) by 20 days.

(21) Appl. No.: 14/423,232

(22) PCT Filed: Aug. 16, 2013

(86) PCT No.: PCT/CA2013/000728
§ 371 (c)(1),
(2) Date: Feb. 23, 2015

(87) PCT Pub. No.: WO2014/032160
PCT Pub. Date: Mar. 6, 2014

(65) Prior Publication Data
US 2015/0223748 A1 Aug. 13, 2015

Related U.S. Application Data

(60) Provisional application No. 61/693,642, filed on Aug. 27, 2012, provisional application No. 61/697,996, filed on Sep. 7, 2012, provisional application No. 61/840,788, filed on Jun. 28, 2013.

(51) Int. Cl.
*A61B 5/00* (2006.01)
*G06K 9/00* (2006.01)
*A61B 5/024* (2006.01)

(52) U.S. Cl.
CPC .......... *A61B 5/4362* (2013.01); *A61B 5/02405* (2013.01); *A61B 5/02411* (2013.01);
(Continued)

(58) Field of Classification Search
CPC ............ A61B 5/4343–5/4362; A61B 5/02405; A61B 5/02411; A61B 5/7246; A61B 5/033; A61B 5/0444
See application file for complete search history.

(56) References Cited

U.S. PATENT DOCUMENTS

| 7,113,819 B2 | 9/2006 | Hamilton et al. |
| 2004/0133115 A1 | 7/2004 | Hamilton et al. |
| 2010/0268124 A1 | 10/2010 | Hamilton et al. |

FOREIGN PATENT DOCUMENTS

WO   WO2014/032160   3/2014

OTHER PUBLICATIONS

International Search Report mailed on Dec. 2, 2013 in connection with International Application No. PCT/CA2013/000728—4 pages.
(Continued)

*Primary Examiner* — Scott Getzow
(74) *Attorney, Agent, or Firm* — Sheridan Ross P.C.

(57) ABSTRACT

A method, and associated apparatus and system, for monitoring a baby in-utero during labor are provided. A fetal heart rate signal and a uterine activity signal are processed to derive fetal well-being information at least in part by i) processing the fetal heart rate signal and the uterine activity signal to model a relationship between uterine activity and fetal heart rate variability; and ii) deriving the fetal well-being information at least in part by processing the modeled relationship. The relationship may be modeled, for example, as a system having the uterine activity signal as an input and fetal heart rate variability as an output. Suitable system identification approaches may be used for modeling such a relationship. A signal for causing the fetal well-being information to be displayed on a display device is released to assist clinicians in identifying whether the baby being monitored is exhibiting an adverse response to hypoxic conditions. In practical systems, the fetal well-being information is derived and displayed over time to convey trends in fetal well-being.

26 Claims, 15 Drawing Sheets

(52) U.S. Cl.
CPC ........... *A61B5/4356* (2013.01); *A61B 5/7246* (2013.01); *G06K 9/00496* (2013.01); *A61B 5/7264* (2013.01)

(56) References Cited

OTHER PUBLICATIONS

Written Opinion of the International Searching Authority mailed on Dec. 2, 2013 in connection with International Application No. PCT/CA2013/000728—5 pages.

International Preliminary Report on Patentability mailed on Nov. 14, 2014 in connection with International Application No. PCT/CA2013/000728—3 pages.

Cerutti S, Civardi S, Bianchi A, Signorini M, Ferrazzi E, Pardi G. Spectral analysis of antepartum heart rate variability. Clin Phys Physiol Meas 1989;10:27-31.

Romano M, Bifulco P, Cesarelli M, Sansone M, Bracale M. Foetal heart rate power spectrum response to uterine contraction. Medical and Biological Engineering and Computing Mar. 2006; 44:88-201.

Signorini M, Magenes G, Cerutti S, Arduini D. Linear and nonlinear parameters for the analysis of fetal heart rate signal from cardiotocographic recordings. IEEE Transactions on Biomedical Engineering 2003; 50(3):365-374. ISSN 0018-9294.

Warrick PA, Hamilton EF, Precup D, Kearney RE. Identification of the dynamic relationship between intra-partum uterine pressure and fetal heart rate for normal and hypoxic fetuses. IEEE Transactions on Biomedical Engineering Jun. 2009; 56(6):1587-1597.

Warrick P, Hamilton E, Precup D, Kearney R. Classification of normal and hypoxic fetuses from systems modeling of intrapartum cardiotocography. IEEE Transactions on Biomedical Engineering 2010;57(4): 771-779. ISSN 0018-9294.

METHOD AND APPARATUS FOR MONITORING A FETUS DURING LABOR

CROSS REFERENCE TO RELATED APPLICATIONS

This application is a national stage application under 35 U.S.C. 371 and claims the benefit of PCT Application No. PCT/CA2013/000728 having an international filing date of Aug. 16, 2013, which designated the United States, which PCT application claimed the benefit of U.S. Provisional Application No. 61/693,642 filed Aug. 27, 2012; U.S. Provisional Application No. 61/697,996 filed Sep. 7, 2012; U.S. Provisional Application No. 61/840,788 filed Jun. 28, 2013, the disclosures of each of which are incorporated herein by reference in their entirety.

FIELD OF THE INVENTION

The present invention relates generally to the field of obstetrics and, more specifically, to a method, computer program products and a system for monitoring a baby in-utero during labor at least in part based on fetal heart rate variability and contraction information. The invention can be used to assist decision making in clinical medicine.

BACKGROUND

Birth related injuries are rare but devastating events because the consequences can lead to lifelong impairment for the baby, family and society in general. During labor, clinical staff monitor various health characteristics of the obstetrics patients in order to obtain a qualitative assessment of the mother's and the fetus's well-being.

Fetal oxygen deprivation during labor and delivery can affect the fetal brain and result in permanent brain injury or even fetal death. A challenge for clinicians caring for women during childbirth is to identify the small number of babies who are experiencing clinically significant hypoxemia in order to intervene before there is progression to fetal brain injury, without causing an excessive number of unnecessary interventions in the great majority of women with normal childbirth. This problem is challenging because clinicians have limited access to the babies during labor and cannot measure fetal brain oxygenation directly.

Various solutions have been proposed to address this challenge. An approach commonly used by clinicians is to rely upon specialized devices that can measure the fetal heart rate and uterine pressure. The fetal heart rate and uterine pressure are then displayed as tracings over time and visually examined by the clinicians to make inferences about the state of the baby. A deficiency with such an approach is that the display of the fetal heart rate over time does necessarily fully reflect the state of the fetal brain and visual inspection has poor resolution of fine details and relationships between the signals.

Heart rate is constantly modulated by the sympathetic nervous system (increasing the heart rate) and parasympathetic nervous system (decreasing the heart rate). These brief changes in the baseline heart rate are known clinically as heart rate variability. Trends in heart rate variability and the degree and duration of minimal or absent variability are considered as material clinical indicators of fetal cerebral state. For instance, persistently low fetal heart rate variability is thought to represent an energy conserving state of the fetal brain in response to hypoxemia or acidemia or to reflect actual brain injury. Experimentation using pharmacologic blocking agents has shown that the parasympathetic nervous system mostly influences the high frequency (HF) or short term component of heart rate variability and the sympathetic nervous system mostly influences the low frequency (LF) or long term component of heart rate variability. Fetal movement is associated with changes in the medium frequency (MF) range. As such, measuring these frequency components of heart rate variability is advantageous clinically because it provides information on specific regions of the brain.

Currently used methods for measuring fetal heart rate variability have limitations. In particular, clinicians typically measure variability by visually inspecting the fetal heart rate tracings using the gridlines on the fetal heart rate monitor paper printout. Following the definition of variability provided by the National Institute of Child Health and Human Development (NICHD) in 1999, a common approach is to measure the amplitude of fluctuations around the baseline fetal heart rate. The baseline fetal heart rate are segments of the recording where the fetal heart rate is relatively constant or flat and is without accelerations (transient increases in the heart rate lasting 15 seconds to a few minutes) or decelerations (transient decreases in the heart rate lasting 15 seconds to a few minutes). The baseline variability is then classified as i) absent—amplitude range undetectable; ii) minimal—amplitude range detectable: 5 beats per minute or lower, iii) moderate: 6-25 beats per minute, or iv) marked: >25 beats per minute. Numerous studies have shown poor levels of agreement on visual estimates of absent or minimal variability. Another deficiency associated with visual inspection to measure heart rate variability is that the human eye can generally not accurately separate and measure the components of heart rate variability across its frequency spectrum. As such, techniques based on visual inspection of a heart rate signal to measure heart rate variability are deficient in that: i) they are limited to a simple measure of FHR excursions around the baseline segments; ii) show poor agreement levels in the presence of low variability; and iii) cannot distinguish between components of fetal heart rate variability in specific frequency bands.

Although some techniques for measuring heart rate variability from a digital heart rate signal have been proposed in the past, measuring fetal heart rate variability alone or its components does not fully resolve the clinicians' challenge to identify which babies are experiencing clinically significant hypoxemia in order to intervene before there is progression to fetal brain injury. In particular, it is noted that while low heart rate variability may be caused by a number of pathological conditions, low heart rate variability may also be caused by benign conditions. In fact, a number of benign conditions can affect heart rate variability such as fetal sleep-wake cycles or medications which are not harmful. Pathological conditions such as remote brain injury earlier during the prenatal period which are not improved by intervention during labor can also cause low heart rate variability. As such existing techniques using fetal heart rate variability may not be adequate for distinguishing between benign and hypoxemic conditions.

In light of the above, there is a need in the industry to provide methods and devices for monitoring a baby in-utero during labor that alleviate at least some of the above identified deficiencies.

SUMMARY

In accordance with a first aspect, the invention relates to a method, and associated apparatus, computer program product and system, for monitoring a baby in-utero during labor which comprises modeling a relationship between uterine activity and fetal heart rate variability for the baby. The modeled relationship provides an indication of how the baby being monitored is responding to hypoxic conditions triggered by uterine activity. Based upon comparisons with reference relationships exhibited by babies that either had adverse responses to hypoxic conditions or by babies that did not, a ranking can be assigned to the modeled relationship to assist clinicians in determining a likelihood that the baby being monitored is exhibiting an adverse response to hypoxic conditions before fetal brain injury occurs.

In accordance with another aspect, the invention relates to a method for monitoring a baby in-utero during labor. The method is implemented by a system including at least one programmable processor and comprises receiving a fetal heart rate signal and a uterine activity signal and processing these signals to derive fetal well-being information at least in part by:
  processing the fetal heart rate signal and the uterine activity signal to model a relationship between uterine activity and fetal heart rate variability;
  deriving the fetal well-being information at least in part by processing the modeled relationship between the uterine activity and the fetal heart rate variability;

The method also comprises releasing a signal for causing the fetal well-being information to be displayed on a display device to assist clinicians in identifying whether the baby being monitored is exhibiting an adverse response to hypoxic conditions.

In accordance with a specific implementation, processing the fetal heart rate signal and the uterine activity signal to model the relationship between uterine activity and fetal heart rate variability includes processing the fetal heart rate signal at least in part to derive fetal heart rate variability measurements. In this specific implementation, the relationship between uterine activity and fetal heart rate variability may be modeled at least in part as a system having the uterine activity signal as an input and the variability measurements as an output.

The system may be associated with a system response derived at least in part by using a system identification approach, wherein the system response is associated with system response parameters. In non-limiting examples of implementations, the system response parameters may include:
  a delay parameter conveying a delay between a rise in uterine pressure conveyed by the uterine activity signal and a change in the fetal heart rate variability;
  a gain parameter conveying an amount of change in the fetal heart rate variability following the rise in uterine pressure;
  a duration parameter conveying a time delay for the fetal heart rate variability to return to its original state following a rise in uterine pressure.

In a specific implementation, the system response may be modeled linearly as an impulse response function using the uterine activity signal as an input and the variability measurements as an output.

In accordance with a specific implementation, the fetal well-being information is derived at least in part by processing the modeled relationship between the uterine activity and the fetal heart rate variability by:
  performing a comparison between the modeled relationship between the uterine activity and the fetal heart rate variability with a set of reference relationships to derive ranking information conveying a degree to which a baby is likely to be having an adverse responses to hypoxic conditions;
  deriving the fetal well-being information at least in part based on the derived ranking information.

At least one of the reference relationships against which the modeled relationship is compared is associated with deliveries in which metabolic acidemia developed and at least another one of the reference relationships is associated with deliveries that were normal.

In accordance with a specific example of implementation, the modeled relationship between uterine activity and fetal heart rate variability may include multiple relationship modeling components associated with respective frequency bands. For example, the modeled relationship between uterine activity and fetal heart rate variability may include:
  a first relationship modeling component for modeling the relationship between the uterine activity and the fetal heart rate variability in a first frequency band; and
  a second relationship modeling component for modeling the relationship between the uterine activity and the fetal heart rate variability in a second frequency band, the second frequency band being distinct from the first frequency band.

In a non-limiting example, the first relationship modeling component may include a first system response associated with a first set of system response parameters and the second relationship modeling component may include a second system response associated with a second set of system response parameters.

In accordance with another aspect, the invention relates to a computer program product, tangibly stored on one or more tangible computer readable storage media, for monitoring a baby in-utero during labor. The program product comprising instructions that, when executed, cause a programmable system including at least one programmable processor to implement a method of the type described above for monitoring a baby in-utero during labor.

In accordance with another aspect, the invention relates to an apparatus for monitoring a baby in-utero during labor. The apparatus comprises at least one input for receiving a fetal heart rate signal and a uterine activity signal and a processor in communication with the at least one input. The processor is programmed for processing the fetal heart rate signal and the uterine activity signal to derive fetal well-being information at least in part by:
  processing the fetal heart rate signal and the uterine activity signal to model a relationship between uterine activity and fetal heart rate variability;
  deriving the fetal well-being information at least in part by processing the modeled relationship between the uterine activity and the fetal heart rate variability;

The apparatus also comprises an output for releasing a signal causing the fetal well-being information to be displayed on a display device to assist clinicians in identifying whether the baby being monitored is exhibiting an adverse response to hypoxic conditions.

In accordance with another aspect, the invention relates to a system for monitoring a baby in-utero during labor. The system comprises a fetal heart rate sensor for generating a fetal heart rate signal and a uterine activity sensor for measuring uterine pressure and generating a uterine activity signal. The system also comprises at least one processor in communication with the fetal heart rate sensor and the uterine activity sensor, the at least one processor being programmed for implementing a method of the type described above for monitoring a baby in-utero during labor.

The system also comprises a display device in communication with the at least one processor.

In accordance with another aspect, the invention relates to a method for monitoring a baby in-utero during labor, the method being implemented by a system including at least one programmable processor. The method comprises processing a fetal heart rate signal and a uterine activity signal to model a relationship between uterine activity and fetal heart rate variability. The method also comprises processing the modeled relationship to assign a ranking based upon reference relationships, wherein:

at least one of the reference relationships is associated with a low likelihood of having an adverse response to hypoxic conditions; and at least another one of the reference relationships is associated with a high likelihood of having an adverse response to hypoxic conditions.

The method also comprises deriving information conveying fetal well-being at least in part using the assigned ranking and presenting the information conveying fetal well-being on a display to assist clinicians in identifying whether the baby being monitored is exhibiting an adverse response to hypoxic conditions.

In accordance with another aspect, the invention relates to a method for monitoring a baby in-utero during labor. The method is implemented by a system including at least one programmable processor and comprises receiving and processing a fetal heart rate signal; to derive fetal well-being information at least in part by:

processing the fetal heart rate signal to derive a quiescent variability measurement conveying a background state of fetal heart rate variability;

deriving the fetal well-being information at least in part by performing a comparison between the quiescent variability measurement and reference quiescent variability measurements to derive ranking information conveying a degree to which the baby being monitored is likely to be having an adverse response to hypoxic conditions;

The method also comprises releasing a signal for causing the fetal well-being information to be displayed on a display device to assist clinicians in identifying whether the baby being monitored is exhibiting an adverse response to hypoxic conditions.

In accordance with a specific implementation, at least one of the reference quiescent variability measurements is associated with deliveries in which metabolic acidemia developed and at least another one of the reference quiescent variability measurements is associated with deliveries that were normal.

In a specific implementation, the derived quiescent variability measurement includes:

a first quiescent variability measurement component associated with a first frequency band;

a second quiescent variability measurement component associated with a second frequency band, the second frequency band being distinct from the first frequency band.

In accordance with another aspect, the invention relates to a computer program product, tangibly stored on one or more tangible computer readable storage media, for monitoring a baby in-utero during labor. The program product comprising instructions that, when executed, cause a programmable system including at least one programmable processor to implement a method of the type described above for monitoring a baby in-utero during labor.

In accordance with another aspect, the invention relates to a system for monitoring a baby in-utero during labor. The system comprises a fetal heart rate sensor for generating a fetal heart rate signal and at least one processor in communication with the fetal heart rate sensor. The at least one processor is programmed for implementing a method of the type described above for monitoring a baby in-utero during labor. The system also comprises a display device in communication with the at least one processor.

In accordance with another aspect, the invention relates to a method for monitoring a baby in-utero during labor. The method is implemented by a system including at least one programmable processor and comprises receiving a fetal heart rate signal and a uterine activity signal. The method also comprises processing the fetal heart rate signal and the uterine activity signal to derive fetal well-being information at least in part by:

processing the fetal heart rate signal and the uterine activity signal to:

model a relationship between uterine activity and fetal heart rate variability; and derive a quiescent variability measurement conveying a background state of fetal heart rate variability;

using the quiescent variability measurement and the modeled relationship between the uterine activity and the fetal heart rate variability to deriving the fetal well-being information.

The method further comprises releasing a signal for causing the fetal well-being information to be displayed on a display device to assist clinicians in identifying whether the baby being monitored is exhibiting an adverse response to hypoxic conditions.

Other aspects and features of the present invention will become apparent to those ordinarily skilled in the art upon review of the following description of specific embodiments of the invention in conjunction with the accompanying Figures.

BRIEF DESCRIPTION OF THE DRAWINGS

Figure 5:
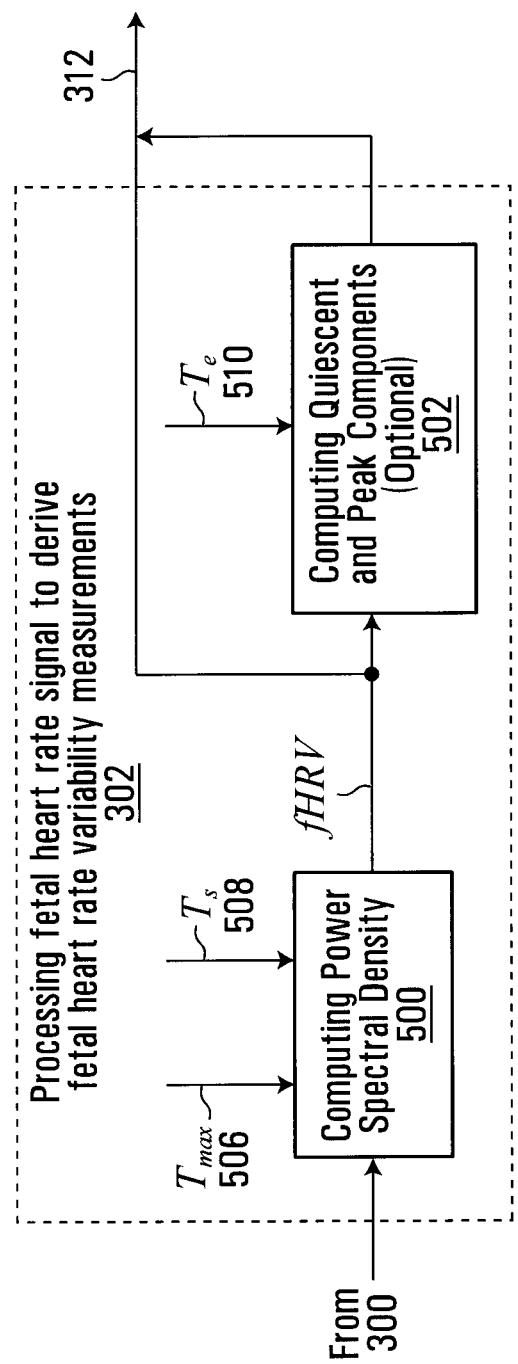
FIG. 5 is a flow diagram of a process for processing a fetal heart rate signal to derive fetal heart rate variability measurements in accordance with a specific example of implementation of the present invention.

A detailed description of examples of implementation of the present invention is provided herein below with reference to the following drawings, in which:

FIG. 6 is a graph showing power density (PSD) estimates for LF (30 to 150 mHz), MF (150 to 500 mHz) and HF (500 to 1000 mHz) bands of fetal heart rate variability measurements derived while applying a process of the type depicted in FIG. 5 to a sample segment of a fetal heart rate signal in accordance with a specific example of implementation of the present invention;

Figure 1:
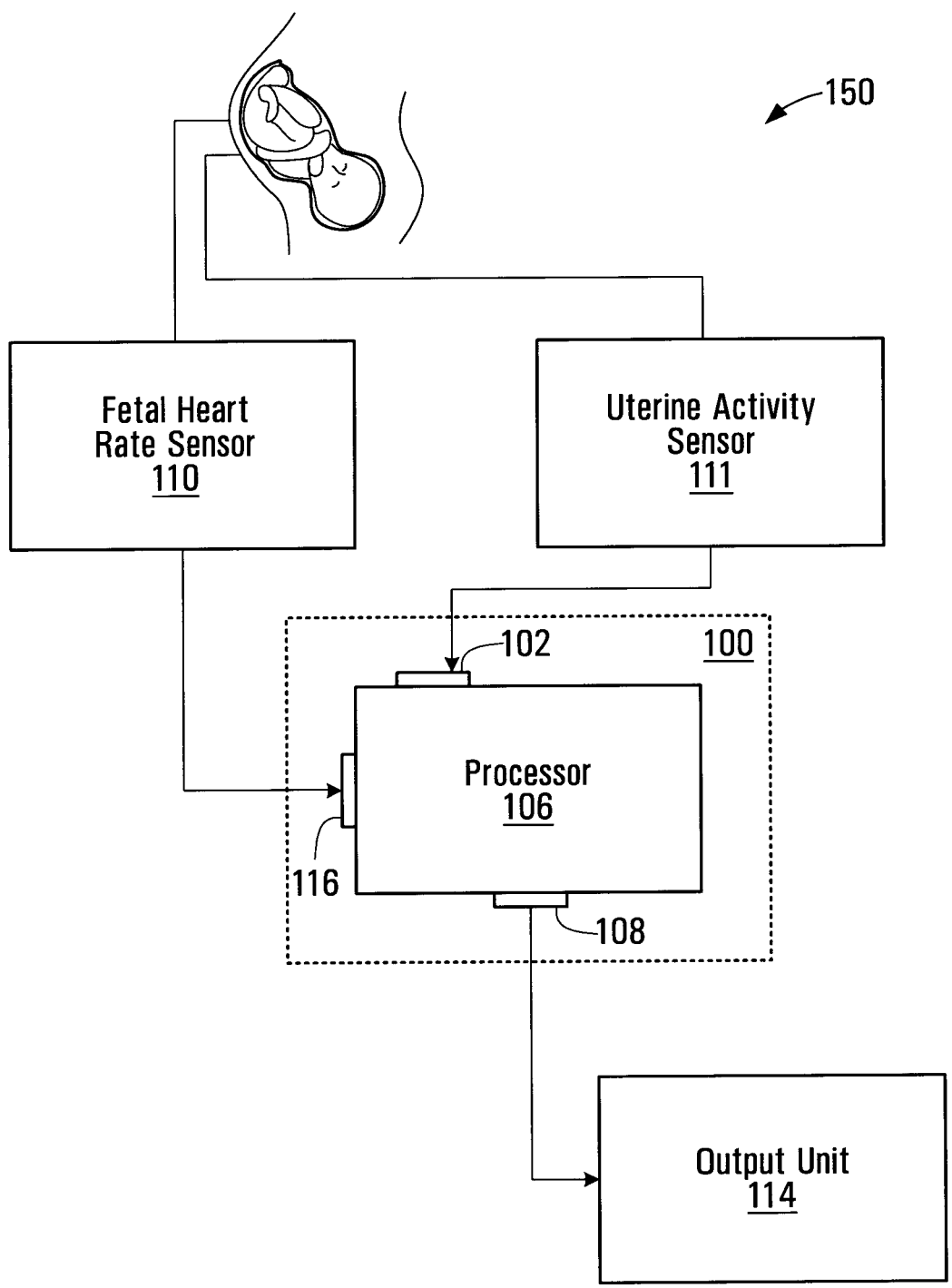
FIG. 1 shows a high-level functional block diagram of a system including an apparatus 100 for monitoring a baby in-utero during labor in accordance with a specific example of implementation of the present invention.
Figure 2:
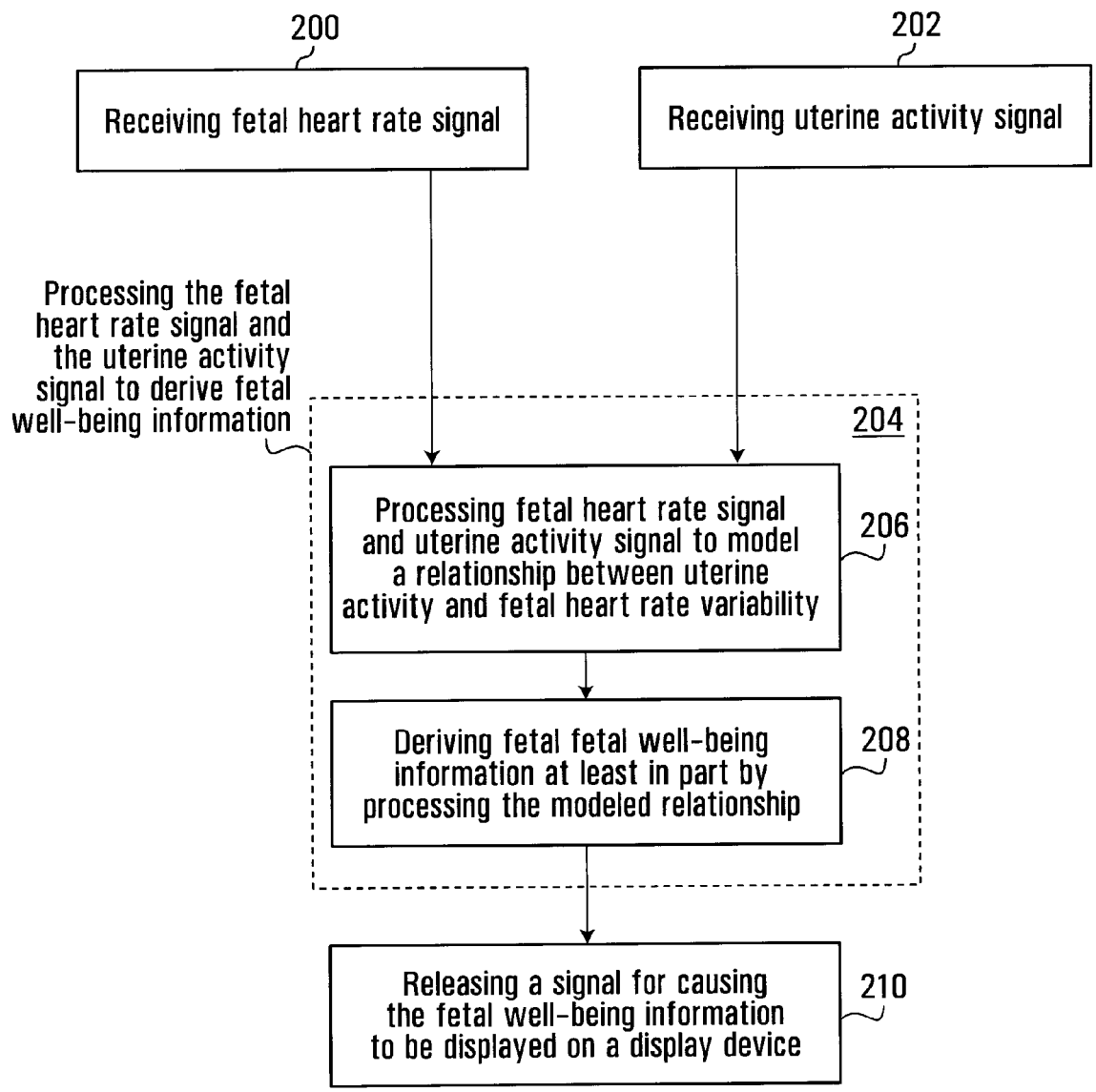
FIG. 2 is a flow diagram implemented by the apparatus 100 for monitoring a baby in-utero during labor of FIG. 1 in accordance with a specific example of implementation of the present invention.
Figure 3:
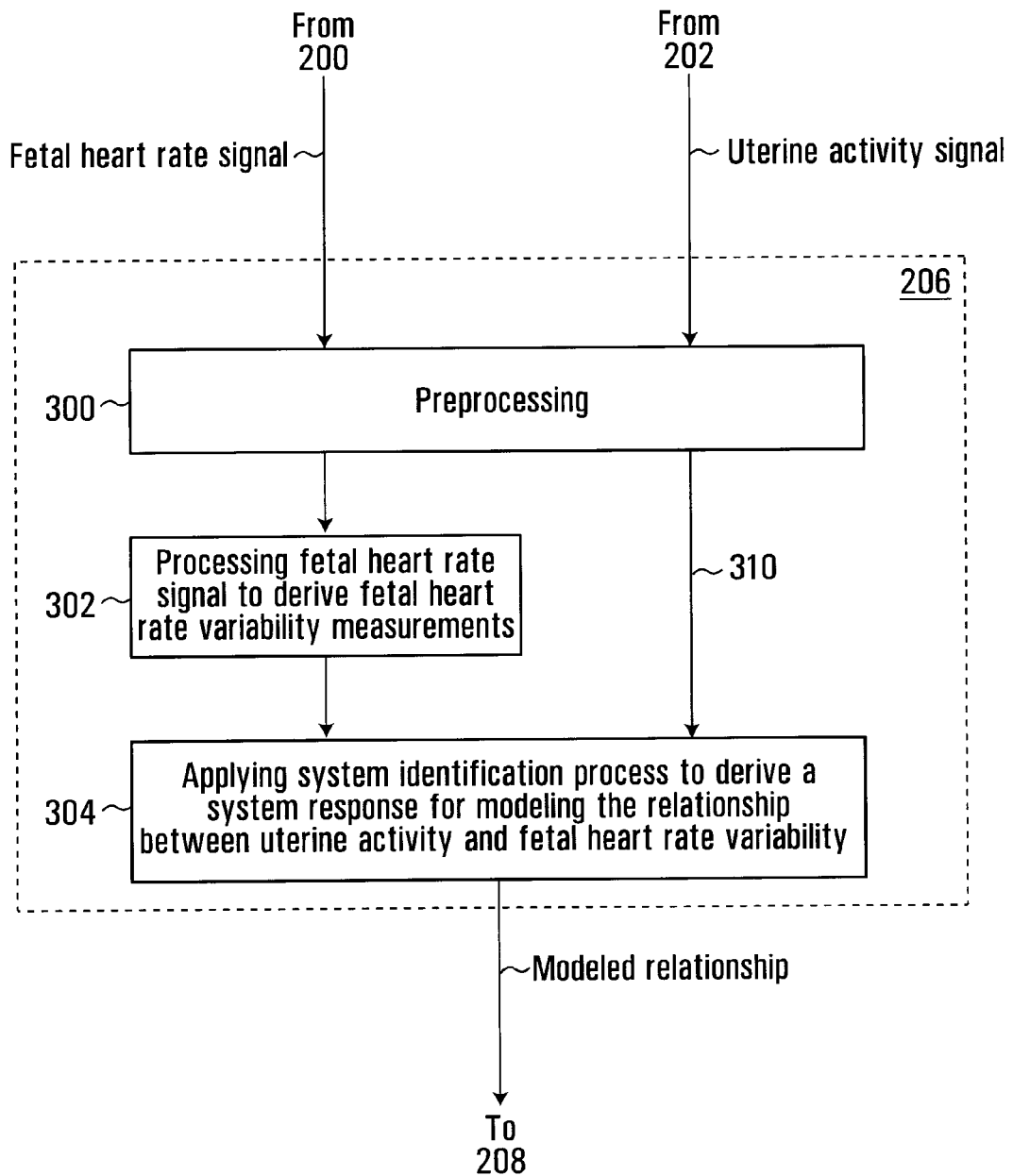
FIG. 3 is a flow diagram of a process, which may be used in connection with the process depicted in FIG. 2, for modeling a relationship between uterine activity and fetal heart rate variability in accordance with a specific example of implementation of the present invention.
Figure 7:
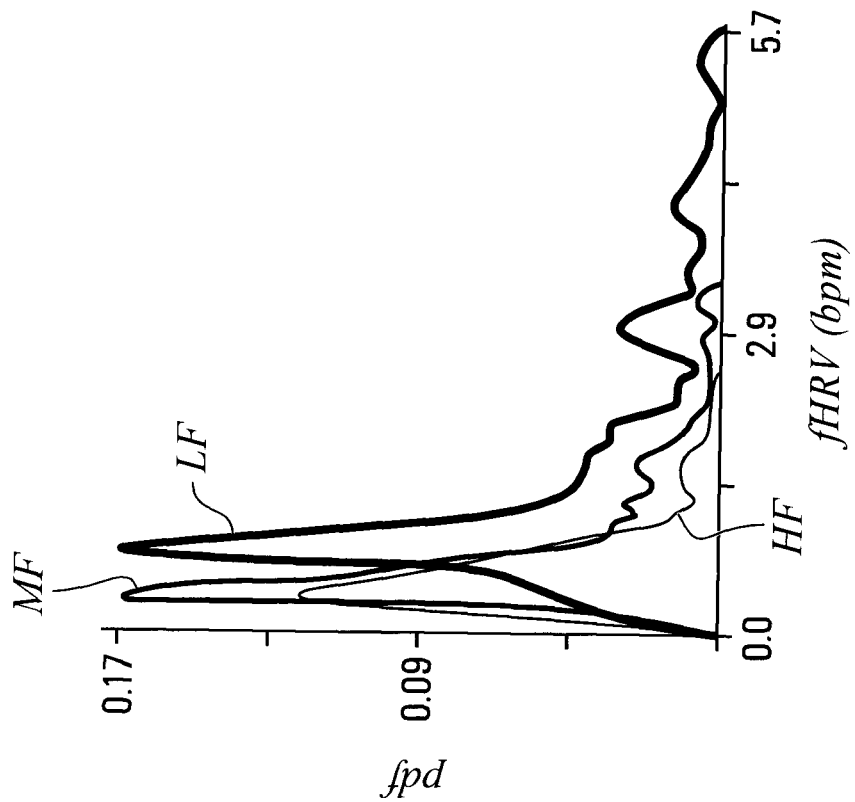
Figure 8:
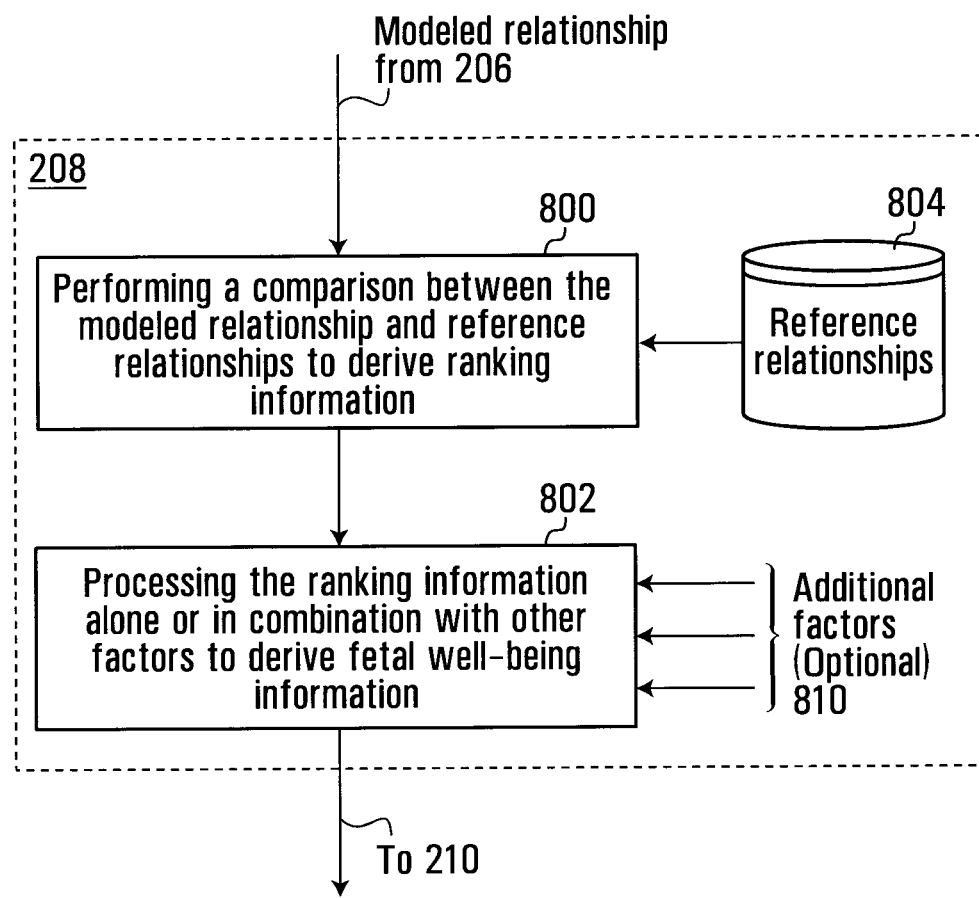
Figure 9:
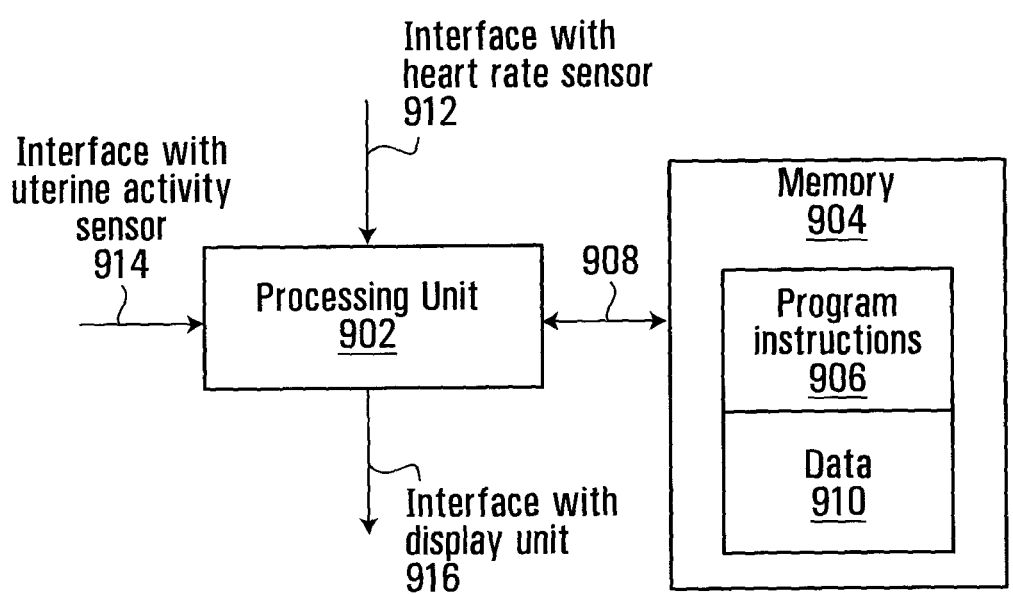
Figure 10:
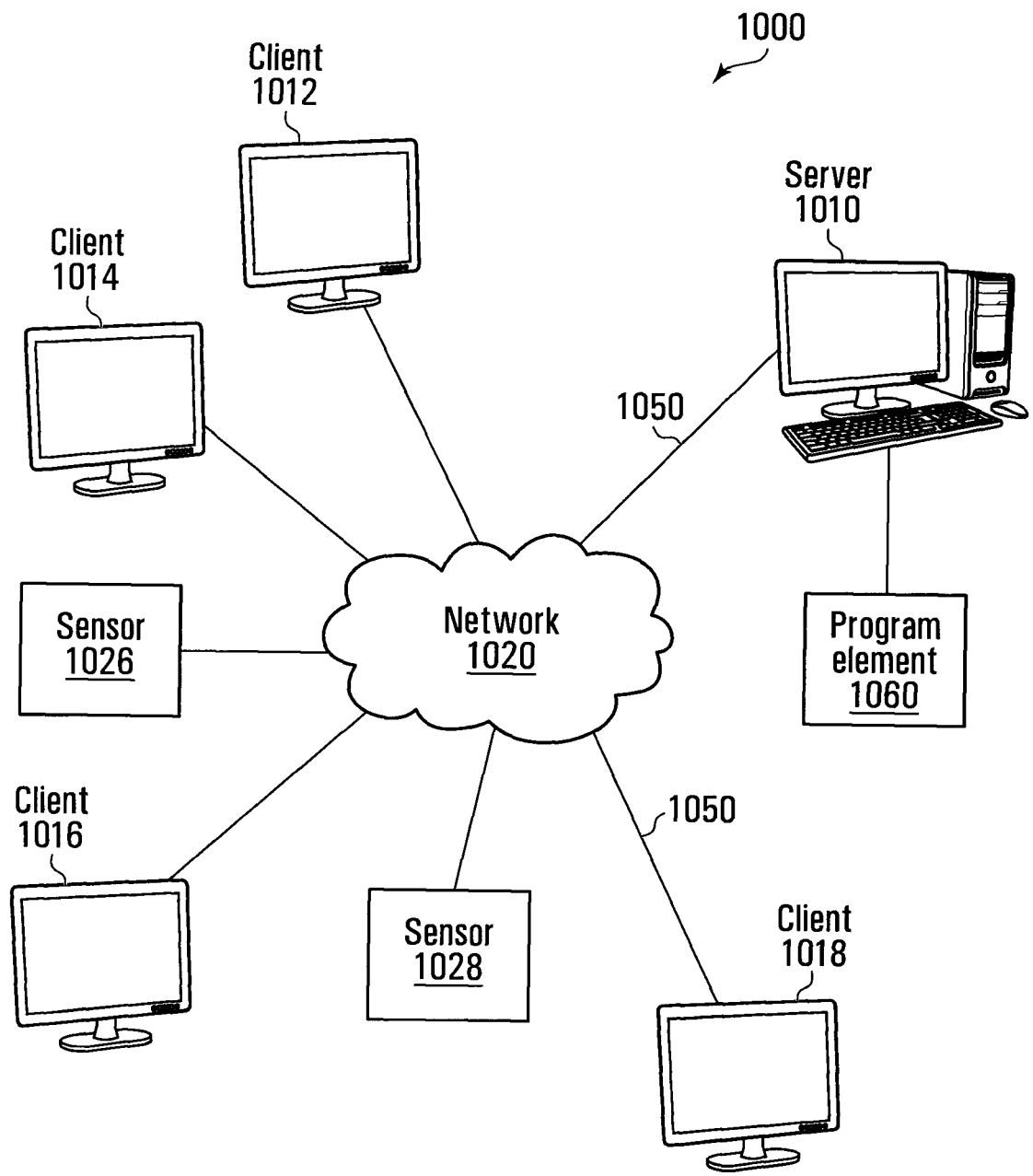
Figure 11:
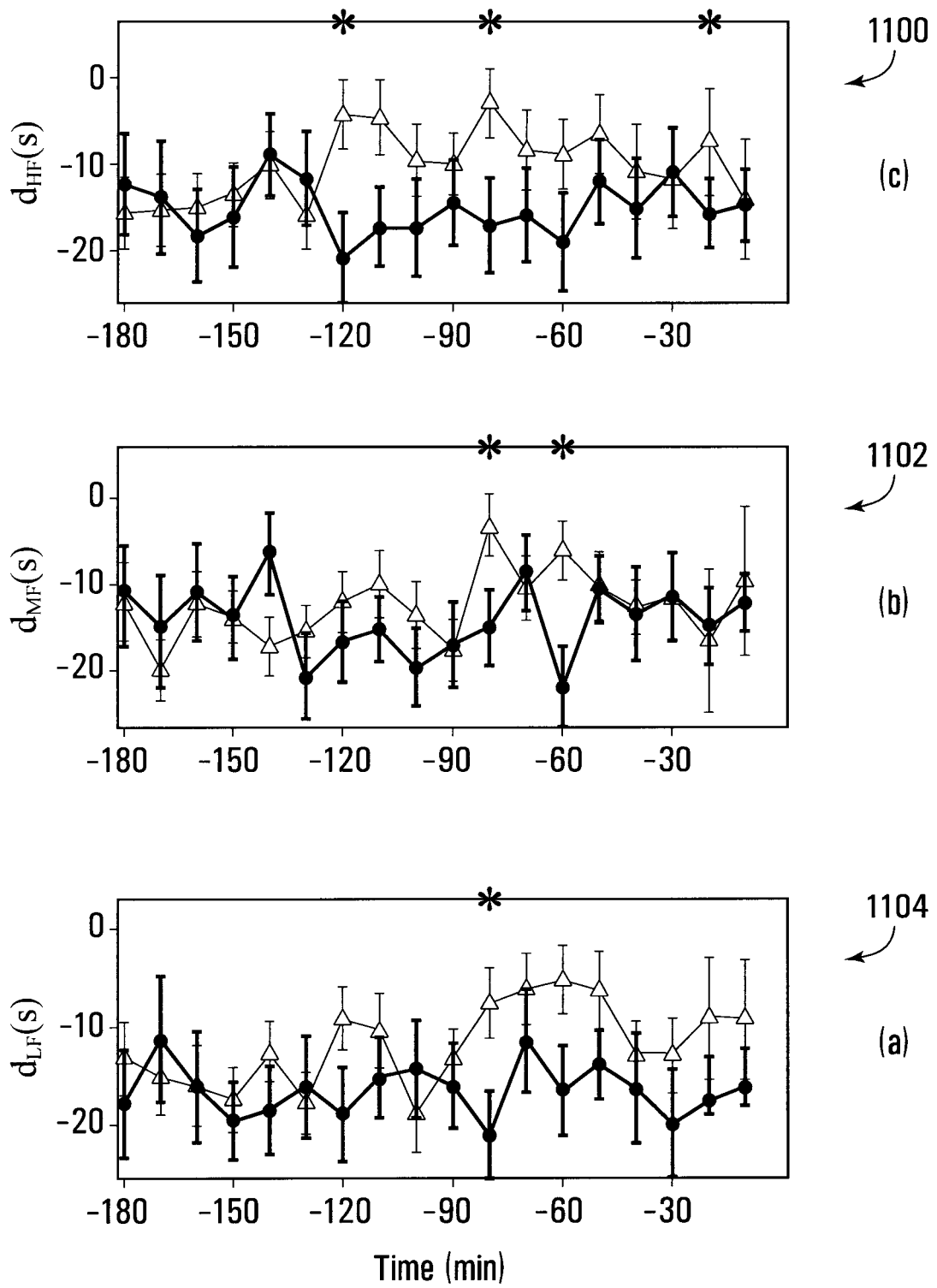
Figure 12:
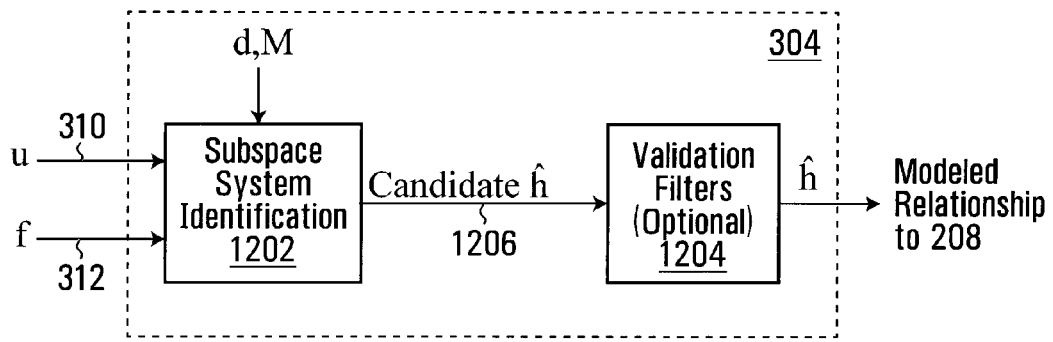
Figure 13:
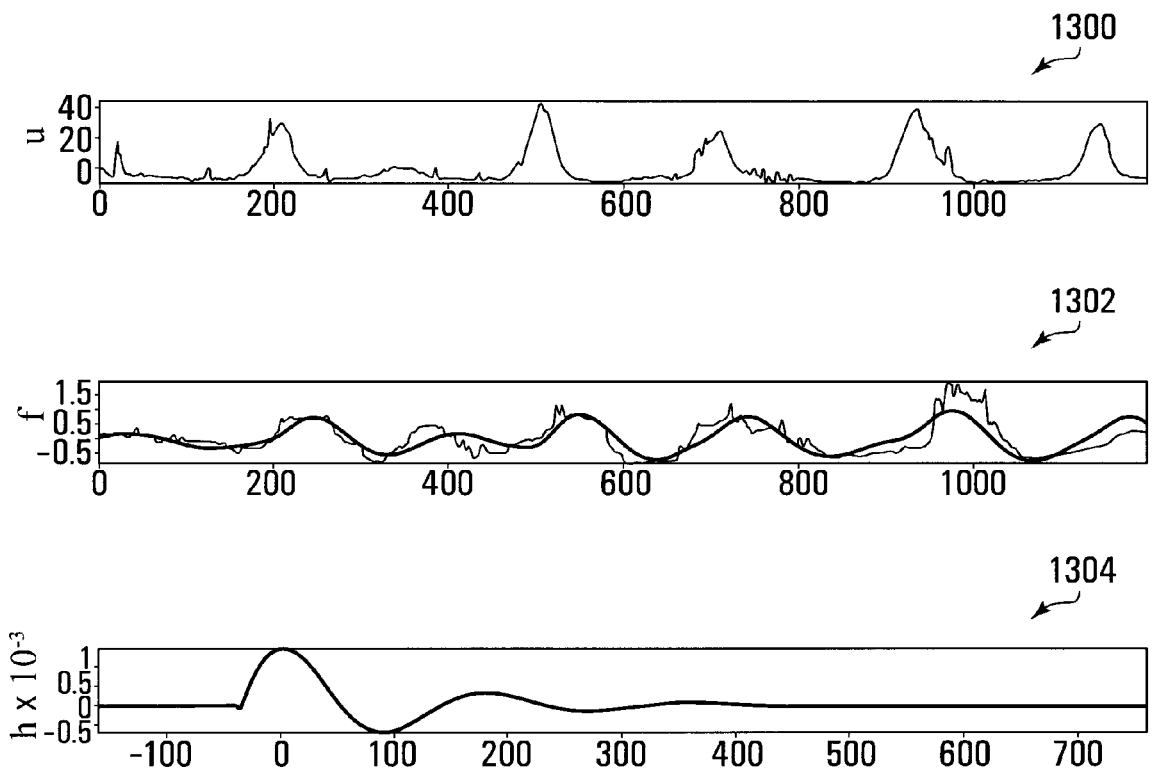
Figure 14:
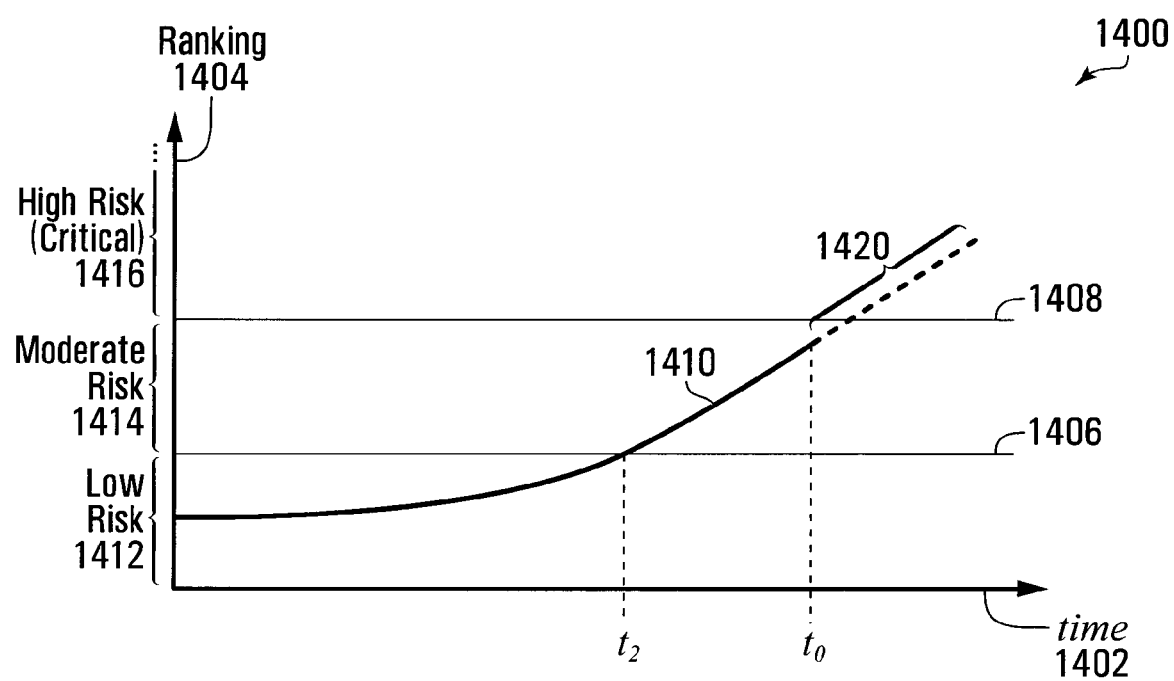
Figure 15:
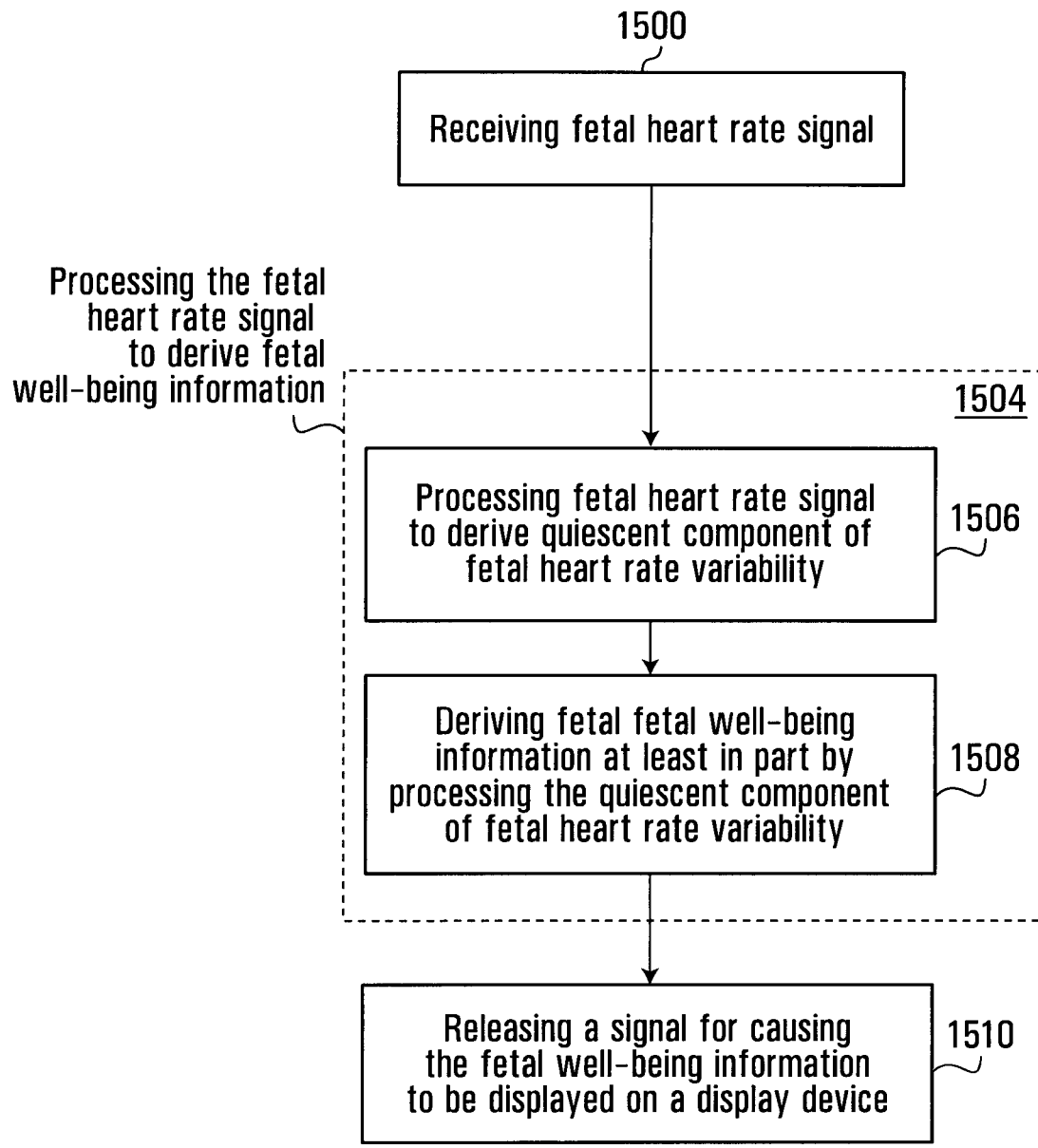
Figure 16:
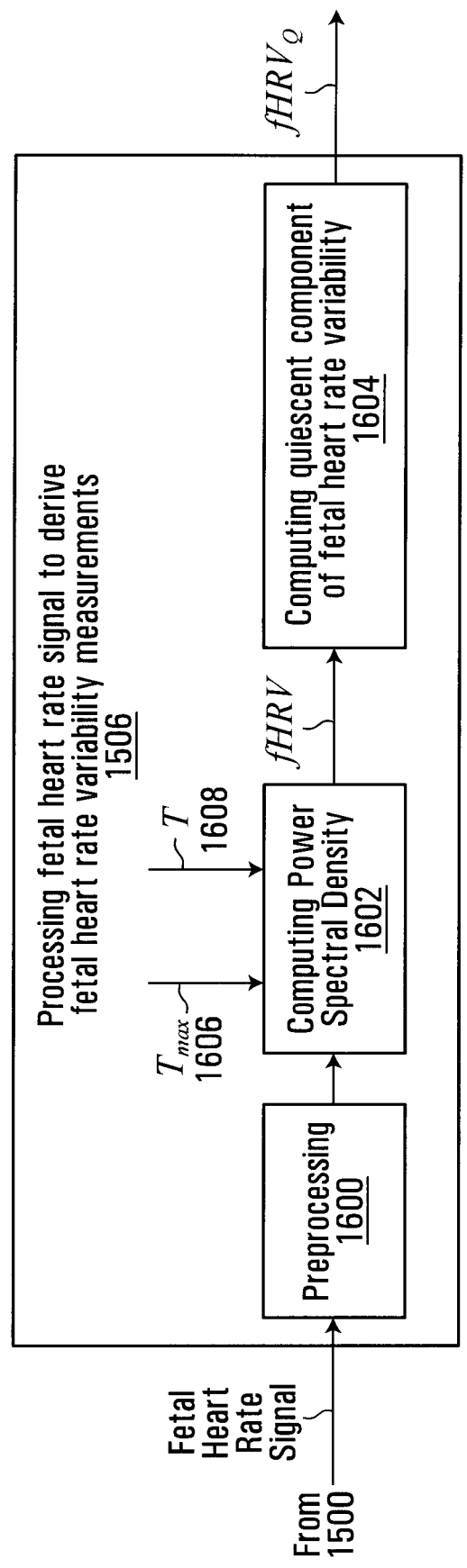
Figure 17:
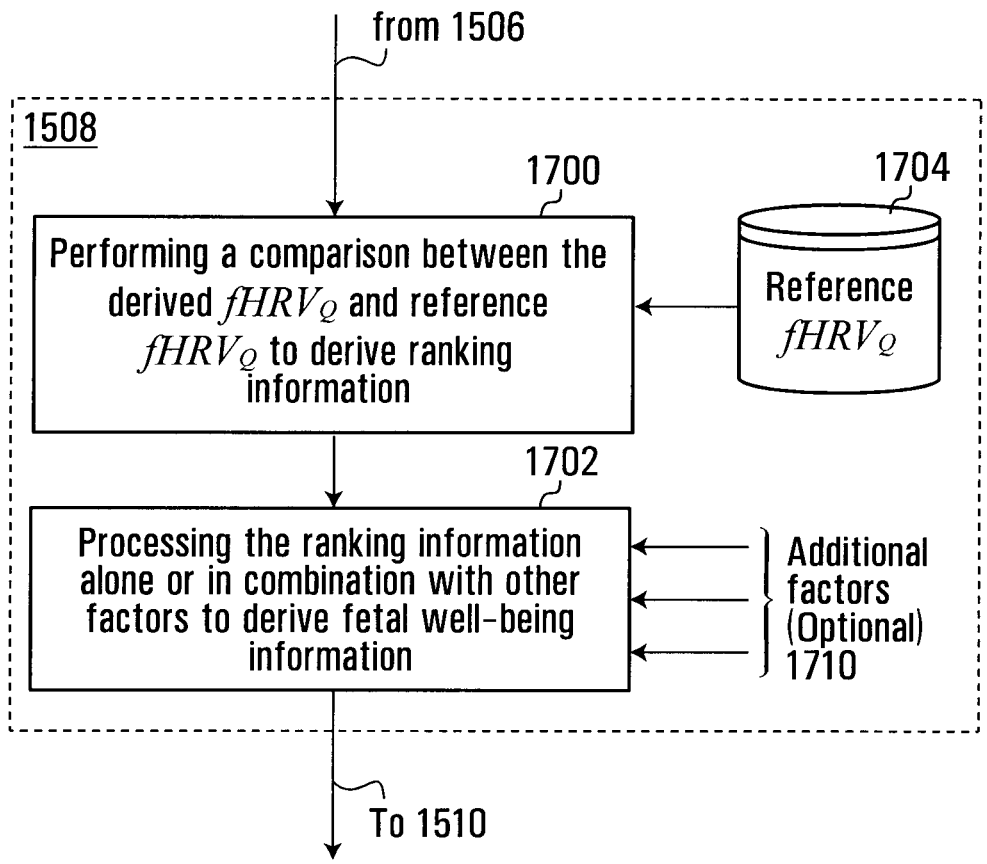

FIG. 7 is a graph showing probability distribution functions (pdfs) of fHRV components for each of the LF, MF and HF bands of fetal heart rate variability derived while applying a process of the type depicted in FIG. 5 to a segment of a fetal heart rate signal in accordance with a specific example of implementation of the present invention;

FIG. 8 is a flow diagram of a process, which may be used in connection with the process depicted in FIG. 2, for deriving fetal well-being information at least in part by processing a modeled relationship between uterine activity and fetal heart rate variability in accordance with a specific example of implementation of the present invention;

FIG. 9 shows a functional block diagram of an apparatus for monitoring a baby in-utero during labor in accordance with a specific example of implementation of the present invention;

FIG. 10 shows a functional block diagram of a client-server system for monitoring a baby in-utero during labor in accordance with an alternative specific example of implementation of the present invention;

FIG. 11 are graphs conveying delays of different impulse response functions (IRF) for two reference groups (one normal and one whether the babies had adverse responses to hypoxic conditions) using uterine pressure as an input and fetal heart rate variability (fHRV) measurements in each of the three bands as outputs: (a) low frequency 1104 (LF) (b) movement frequency (MF) 1102 and (c) high frequency (HF) 1100 in accordance with a specific example of implementation of the present invention;

FIG. 12 shows a process, which may be used in connection with the process depicted in FIG. 3, for performing system identification using a linear approach for deriving an impulse response function (IRF) in accordance with a specific example of implementation of the present invention;

FIG. 13 are graphs conveying a (preprocessed) uterine activity signal (u), fetal heart rate variability measurements in the movement frequency band (fHRV$_{MF}$) (f) (shown in the thin line in 1302), the model-predicted fetal heart rate variability measurements (shown in the thick line in 1302) and a derived impulse response function (IRF) (hx10$^{-3}$) in accordance with a specific example of implementation of the present invention;

FIG. 14 is a graph conveying fetal well-being information for assisting clinicians in identifying whether a baby being monitored is exhibiting an adverse response to hypoxic conditions in accordance with a specific non-limiting example of implementation of the present invention;

FIG. 15 is a flow diagram implemented by the apparatus 100 for monitoring a baby in-utero during labor of FIG. 1 in accordance with a specific example of implementation of another aspect of the present invention;

FIG. 16 is a flow diagram of a process, which may be used in connection with the process depicted in FIG. 15, for processing a fetal heart rate signal to derive fetal heart rate variability measurements in accordance with a specific example of implementation of the present invention;

FIG. 17 is a flow diagram of a process, which may be used in connection with the process depicted in FIG. 15, for deriving fetal well-being information at least in part by processing a quiescent component of fetal heart rate variability fHRV$_Q$ in accordance with a specific example of implementation of the present invention.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

During uterine contractions the tightening of the myometrial muscle constricts arterial blood vessels and causes a reduction in perfusion to the placenta and hence oxygen delivery to the baby. In general, these intermittent changes are within the physiological ranges and well tolerated by the baby. In other situations, contractions may be associated with inordinate decreases in oxygen delivery such as in the presence of excessively strong and frequent contractions or a malfunctioning placenta. In addition, babies have different compensatory capacities. Some babies will not tolerate even small contractions with its resulting minor hypoxemia, whereas others will tolerate long periods of overly frequent and strong contractions.

In the present application, it is suggested to measure the fetal heart rate variability response relative to contractions in order to obtain information about how the baby is reacting to the contractions both in terms of fetal compensatory capacity and fetal cerebral state. In addition, by obtaining such measurements over time and conveying the progression of these measurements, an indication may be obtained of whether a baby is showing increasingly adverse responses to hypoxic conditions and is likely to progress to brain injury.

With reference to FIG. 1, there is shown a configuration of a system 150 for monitoring a baby in-utero during labor. The system includes a fetal heart rate sensor 110, a uterine activity sensor 111, an apparatus 100 implementing tools for monitoring a baby in-utero during labour and an output unit 114 for conveying information derived by the apparatus 100.

The fetal heart rate sensor 110 is for detecting a fetal heart rate of a baby in-utero, also referred to as a fetus in the womb. In a specific implementation, the fetal heart rate sensor 110 samples the fetal heart rate at a certain pre-determined frequency to generate a fetal heart rate signal. In a specific non-limiting implementation, the fetal heart rate sensor 110 is configured to sample the fetal heart rate at a uniform sampling rates of 4 Hz (measured in beats per minute (bpm)) however it is to be appreciated that the fetal heart rate sensor used in alternative implementations may sample the heart rate at any other suitable sampling rate. Fetal heart rate sensors are well known in the art to which this invention pertains and as such will not be described further here.

The uterine activity sensor 111 is for monitoring uterine activity (TOCO). The sensor 111 samples the uterine pressure at a certain pre-determined frequency to generate a uterine activity signal. In a specific non-limiting implementation, the uterine activity sensor 111 is configured to sample uterine pressure at a uniform sampling rate of 1 Hz (measured in mmHg). The uterine pressure sampled at 1 Hz can optionally be up-sampled to 4 Hz by zero-insertion and low-pass filtering. Sensors for monitoring uterine activity are well known in the art to which this invention pertains and as such will not be described further here.

Optionally, the system 150 may further include a user input device (not shown) for receiving data from a user of the system. The data may convey commands directed to controlling various features of the tools implemented by apparatus 100 and, optionally, may also convey various measurements taken during labor and associated with the obstetrics patients, such as for example (but not limited to) cervical dilation measures and levels of fetal descent. The type of data received through such a user input device may vary depending on the type of information that the apparatus 100 is adapted to process and interpret. The user input device may include any one or a combination of the following: keyboard, pointing device, touch sensitive surface, actuator/selection switches or speech recognition unit.

Optionally still, the fetal monitoring system 150 may further include other sensors (not shown) for measuring labor progress and the baby's tolerance to labor. Such sensors may include, for example but not limited to, a sensor for measuring the maternal oxygen saturation and a sensor for measuring maternal blood pressure. The specific manner in which data generated using these other sensors (or data obtained through a user input device) may be used in assessing labor progress and the baby's tolerance to labor is beyond the scope of the present application and thus will not be described further here. The person skilled in the art will however appreciate that the methods and approaches presented in the present application may be used alone or in combination with other methods and approaches to generate information for assisting clinical staff in assessing labor progress and the baby's tolerance to labor.

The output unit 114 is in communication with the apparatus 100 and receives signals causing the output unit 114 to convey information by apparatus 100. The output unit 114 may be in the form of a display screen, a printer or any other suitable device for conveying to the physician or other health care professional information conveying fetal well-being during labor and assisting them in identifying whether the baby being monitored is exhibiting an adverse response to hypoxic conditions. In a non-limiting implementation, the output unit 114 includes one or more display monitors to display information derived by the apparatus 100 in a visual format. In non-limiting examples, the display monitor may be a computer screen associated with a computer workstation, the display screen of a computer tablet or the display screen of smart-phone. Alternatively, the output unit 114 may include a printer device for providing a paper print out conveying information derived by the apparatus 100.

The apparatus 100 includes a first input 116, a second input 102, a processor 106 and an output 108. The first input 116 is for receiving a fetal heart rate signal from the fetal heart rate sensor 110 and the second input 102 is for receiving a uterine activity signal from the uterine activity sensor 111. It will be readily appreciated that, although the fetal heart rate signal and the uterine activity signal are shown as being received at two distinct inputs 102 and 116 in the embodiment illustrated in the figures, the signals may be provided to processor 106 either through a same physical input or through separate physical inputs. The processor 106 is programmed to process the fetal heart rate signal and the uterine activity signal to derive information related to fetal well-being. The processor 106 is also programmed to release a signal at output 108 for causing output unit 114 to display the derived information related to fetal well-being to assist clinicians in identifying whether the baby being monitored is exhibiting an adverse response to hypoxic conditions.

Specific examples of the manner in which the information related to fetal well-being may be derived by apparatus 100 will be described in greater detail below with reference to FIG. 2.

FIG. 2 shows a process implemented by the apparatus 100 for monitoring a baby in-utero during labor in accordance with a specific example of implementation.

At step 200, a fetal heart rate signal obtained from the fetal heart rate sensor 110 (shown in FIG. 1) is received. In a specific example of implementation, the fetal heart rate signal received at step 200 conveys samples of the heart rate signal.

At step 202, a uterine activity signal obtained from the uterine activity sensor 111 (shown in FIG. 1) is received. In a specific example of implementation, the uterine activity signal received at step 202 conveys samples of the uterine pressure (UP).

Following receipt of the signals at steps 200 and 202, the process proceeds to step 204.

At step 204, the fetal heart rate signal and the uterine activity signal are processed by to derive fetal well-being information. In the specific example of implementation depicted, the processing of the fetal heart rate signal and the uterine activity signal is shown as comprising at least two steps, namely: a) step 206, where the fetal heart rate signal and the uterine activity signal are processed to model a relationship between uterine activity and fetal heart rate variability; and then b) step 208, where fetal well-being information is derived at least in part by processing the modeled relationship between the uterine activity and the fetal heart rate variability resulting from step 206. The specific manner in which steps 206 and 208 may be put into practice in practical implementations will be described later on in the present document with reference to FIG. 3 and FIG. 8 respectively. Following step 204, the process proceeds to step 210.

At step 210, a signal for causing the fetal well-being information derived by step 204 to be conveyed by output unit 114 (shown in FIG. 1) is released at output 108 (also shown in FIG. 1). In a specific example in which the output unit 114 includes a display device, the signal released causes information to be conveyed on the display device to assist clinicians in identifying whether the baby being monitored is exhibiting an adverse response to hypoxic conditions. The specific manner in which such information may be conveyed may vary from one implementation to the other and may depend on many factors including for example preferences of the clinical staff and/or medical establishments.

In a specific example of implementation, the fetal well-being information conveyed by output unit 114 may convey a ranking indicating a degree to which (or likelihood that) the baby's response is exhibiting a pattern that indicates an adverse response to hypoxic conditions. For example, the ranking may be conveyed as a numerical value in a range between 1 and 10, wherein:

"1" indicates a very low likelihood that the baby is having an adverse response to hypoxic conditions;
"10" indicates a very high likelihood that the baby is having an adverse response to hypoxic conditions; and
the values of ranking going from 1 and 10 indicate an increasing likelihood that the baby is having an adverse response to hypoxic conditions.

Alternatively the ranking may be conveyed using a color scheme where different colors (or color intensities) are associated with different likelihood levels that the baby's response is exhibiting a pattern that indicates an adverse response to hypoxic conditions.

The fetal well-being information may convey a ranking for one time segment (or epoch) of the fetal heart rate and uterine activity signals (either the most recent segment or a segment selected by the user of the system 150 of FIG. 1) or, alternatively, may convey multiple rankings derived over time in order to conveying to clinical staff how the rankings are evolving over time. In a specific practical system, the fetal well-being information is derived and displayed over time to convey trends in fetal well-being. For example, displaying rankings over multiple time periods may allow the clinical staff to ascertain whether the rankings are conveying increasingly higher likelihoods that the baby is having an adverse response to hypoxic conditions, which would indicate that the situation may be deteriorating and that the baby may be likely to progress to injury. Conversely, if the rankings appear to be remaining relatively constant, this may convey to the clinical staff that the situation is likely to be stable.

FIG. 14 shows a graph conveying fetal well-being information for assisting clinicians in identifying whether a baby being monitored is exhibiting an adverse response to hypoxic conditions in accordance with a specific non-limiting example of implementation of the present invention. In this example, the fetal well-being information is conveyed in a graph 1400 where the horizontal axis 1402 is associated with time and the vertical axis is associated with a ranking. In this example, the vertical axis for the ranking is also divided into three segments associated with respective levels of risk namely a low risk segment 1412, a moderate risk segment 1414 and a high risk segment 1416. The segments 1412 1414 and 1416 are defined by thresholds 1406 and 1408. The derived rankings obtained from the fetal heart rate and uterine activity signals are shown over time as a tracing 1410. In this example, the tracing shows that at the beginning, and until about time $t_2$, the rankings conveyed a low likelihood that the baby is having an adverse response to hypoxic conditions. Between time $t_2$ and the current time $t_o$, the rankings are increasing and the risk is now considered to be moderate. Optionally, the display may convey a projection of a possible evolution of the rankings based on recent trends. In the example shown in FIG. 1400, this is shown by segment 1420 depicted in dotted lines showing that the rankings may evolve to the high risk segment 1416. In the current example, the segment 1420 was derived using a linear interpolation taken over rankings obtained in a preceding time period.

It is to be appreciated that the specific manner in which fetal well-being information may be conveyed shown in FIG. 14 was provided only for the purpose of illustration and that many other ways of conveying and displaying such information are possible, which will become apparent to the person skilled in the art in light of the present description.

It is also to be appreciated that, in practical system, the rankings over time conveying degrees to which (or likelihood that) the baby's response is exhibiting a pattern that indicates an adverse response to hypoxic conditions, may be used alone or in combination with other measurements/metrics obtained during labour to provide clinical staff with a more complete indication of how labour progressing. Such additional measurements/metrics may be displayed concurrently with the rankings on output unit 114 (shown in FIG. 1) to allow clinical staff to get a more complete picture of the situation or may be combined with the rankings to yield another (compound) metric. Such additional measurements/metrics are beyond the scope of the present document and thus will not be described in further detail here.

Modeling a Relationship between Uterine Activity and Fetal Heart Rate Variability FIG. 3 is a flow diagram showing in greater detail a manner in which step 206 of the process depicted in FIG. 2 may be implemented for modeling a relationship between uterine activity and fetal heart rate variability in accordance with a specific example of implementation of the present invention.

At step 300, the fetal heart rate signal and the uterine activity signal (received at steps 200 and 202 shown in FIG. 2) are pre-processed in order to segment the fetal heart rate and uterine activity signals into time segments or epochs. In a non-limiting implementation, the time segments have durations of about twenty (20) minutes however it is to be understood that any suitable time duration may be used in alternate implementations. For example, suitable time durations may be in the range of about 10 to about 30 minutes, preferably about 15 to about 25 minutes and most preferably about 17 to about 20 minutes.

The pre-processing at step 300 also includes cleaning the fetal heart rate and uterine activity signals to remove from these signals undesirable artifacts including noise. In particular, it is noted that the heart rate and uterine activity signals are recorded in a clinical setting and therefore are subject to different types of noise. For example, the loss of sensor contact (of either the fetal heart rate sensor 110 or uterine activity sensor 111) can temporarily interrupt the fetal heart rate or the uterine activity signals, and interference from the (much lower frequency) maternal heart rate can corrupt the fetal heart rate signal. Frequently, these types of noise appear in the signals as sharp drops to much lower amplitude followed by a sharp signal restoration. At least one of the objectives of the pre-processing step 300 is to reduce the effect of such types of noise on the resulting signal. Any suitable known signal processing technique for removing/reducing the effect of noise on a signal may be used in connection with pre-processing step 300 in practical embodiments. In a non-limiting example of implementation, linear interpolation is used on the fetal heart rate and the uterine activity signals to bridge interruptions caused by a loss of sensor contact. In addition, in the non-limiting example of implementation, the fetal heart rate signal is detrended by a high-pass filter with cutoff frequency 30 mHz, generally corresponding to the lower limit of the low frequency band of fetal heart rate variability, and is decimated to 2.0 Hz to include the 1.0 Hz upper limit of the HF band of fetal heart rate variability (fHRV). For additional information regarding example of the manner in which these signals may be pre-processed, the reader is invited to refer to P. A. Warrick, E. F. Hamilton, D. Precup, and R. Kearney, "Classification of normal and hypoxic fetuses from systems modeling of intrapartum cardiotocography," *IEEE Transactions on Biomedical Engineering*, vol. 57, no. 4, pp. 771-779, 2010. The contents of the aforementioned document are incorporated herein by reference. It is noted that while the pre-processing of the fetal heart rate and uterine activity signals has been shown as being implemented by apparatus 100 (shown in FIG. 1) in the particular embodiment described, it is to be appreciated that such pre-processing may alternately be performed by the fetal heart rate sensor 110 and uterine activity sensor 111 or by a device external to the apparatus 100. In such alternate embodiments, the preprocessing applied to these signals at step 300 may be omitted. Once the fetal heart rate and the uterine activity signals have been preprocessed, the process proceeds to step 302.

At step 302, the (pre-processed) heart rate signal is processed to derive fetal heart rate variability (fHRV) measurements. The fetal heart rate variability (fHRV) measurements convey, for example, measurements of heart rate variability in one or more frequency bands. The one of more frequency bands may include one, two or more frequency bands depending on the implementation.

In a specific example of implementation, the fetal heart rate variability (fHRV) measurements are derived from the fetal heart rate signal by applying an autoregressive model to estimate the power spectral density (PSD) of the fetal heart rate variability. The fetal heart rate variability measurements may consider the fetal heart rate variability as a whole (all frequency components combined) or may separate the fetal heart rate variability into individual frequency components. In a very specific implementation, the power spectral density (PSD) of the fetal heart rate variability (fHRV) is integrated over three frequency bands to obtain three instantaneous components of fHRV namely:

1. a low frequency (LF) component—(30 to 150 mHz).
2. a medium or movement frequency (MF) component—(150 to 500 mHz); and
3. a high frequency (HF) component—(500 to 1000 mHz);

It is to be appreciated that the number of frequency bands and their boundaries noted above have been shown for the purpose of illustration only and a different number of bands and/or different boundaries may be used in alternate practical implementations.

For additional information on a specific approach that may be used for deriving a fetal heart rate variability (fHRV) measurements, the reader is invited to refer to P. A. Warrick and E. F. Hamilton, "Fetal heart-rate variability response to uterine contractions during labour and delivery," in Computing in Cardiology, vol. 39, 2012, pp. 417-420. The contents of the aforementioned document are incorporated herein by reference. It is to be appreciated that, in the specific examples of implementation of the present invention, the fetal heart rate variability (fHRV) measurements are derived by processing not only portions of the fetal heart rate signal corresponding to baseline (flat portions of the fetal heart rate recording that do not include accelerations or decelerations) but also by processing portions of the fetal heart rate signal corresponding to accelerations and/or decelerations. It is noted that some effects of contractions on the fetal heart rate will be reflected in the deceleration and acceleration segments of the fetal heart rate signal. By accounting for the behaviour of the fetal heart rate variability in these (acceleration and deceleration) segments, in addition to the behaviour of the fetal heart rate variability during baseline segments, a more complete assessment of the manner in which the baby is responding to uterine activity can be obtained. Furthermore, due to the limitations of visual inspection clinicians cannot reliably measure heart rate variability during accelerations and decelerations. Thus transient changes within accelerations or decelerations that are often provoked by changes in uterine pressure cannot be measured accurately with the human eye.

FIG. 5 of the drawings illustrates in greater detail a specific manner in which a fetal heart rate variability (fHRV) measurements may be derived at step 302.

As shown, at step 500, the (pre-processed) heart rate signal is processed to estimate the power spectral density (PSD). In a specific example, power spectral density (PSD) estimates may be computed using a short term ($T_{max}$=1 min—shown as item 506 in the figure) autoregressive models constructed at $T_s$=1 s (increments shown as 508 in the figure). In a non-limited example, a linear prediction of the power spectral density (PSD) may be computed using the Levinson-Durbin algorithm and a model of order p using a minimum-description length (MDL) criterion. For addition information on autoregressive models, the reader is invited to refer to Warrick P, Hamilton E, Precup D, Kearney R. "*Classification of normal and hypoxic fetuses from systems modeling of intrapartum cardiotocography*". IEEE Transactions on Biomedical Engineering 2010; 57(4):773-779.

ISSN 0018-9294. The contents of the aforementioned document are incorporated herein by reference. In a practical implementation, an autoregressive model similar to the one used in the above mentioned document was used except that all intervals that were "bridged" using linear interpolation in the pre-processing step 300 (to account for interruptions in the data) were excluded from consideration in the autocorrelation estimation to reduce bias introduced by the linear interpolation. In other words, the conventional calculation of a fetal heart rate (FHR) autocorrelation estimate $r_f$ was modified to exclude the intervals where the fetal heart rate signal had been interpolated in the pre-processing step 300. Mathematically, the revised calculation for the autocorrelation for a segment of n samples can be expressed as follows:

$$r_f(k) = \frac{1}{n_k}\sum_{i=0}^{n-1}\sum_{k=0}^{N-1} f(i)f((i-k)) \qquad (1)$$

where N is the longest lag and each term $f(i)f(i-k)$ is included in the sum if and only if both $f(i)$ and $f(i-k)$ are non-interpolated samples of the fetal heart rate signal and $n_k$ is the total number of $f(i)f(i-k)$ terms included at lag k.

Figure 6:
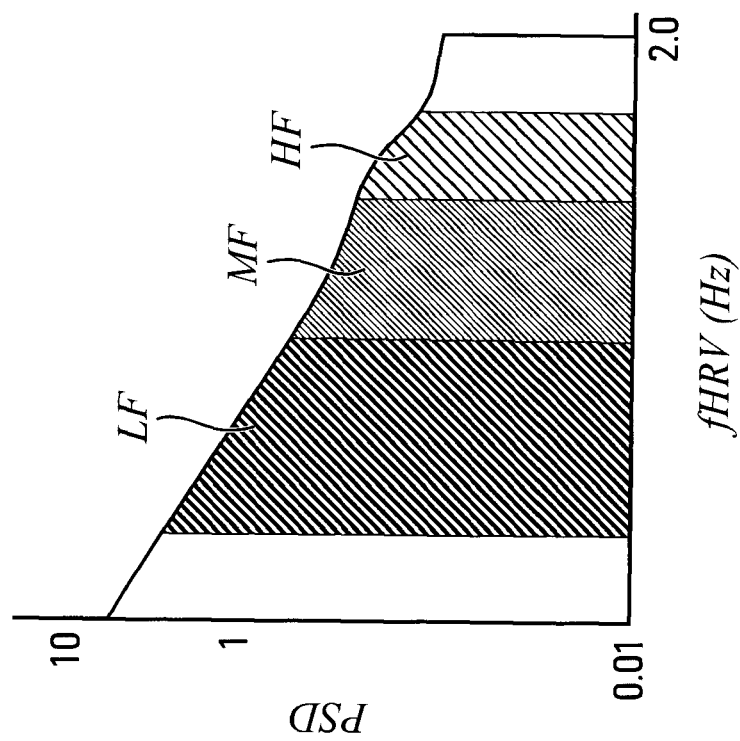

Power spectral densities (PSD) of the autoregressive models can be computed using any suitable approach. In a specific implementation, the PSD of the autoregressive model may be computed in a manner similar to that described in Cerutti S, Civardi S, Bianchi A, Signorini M, Ferrazzi E, Pardi G. "*Spectral analysis of antepartum heart rate variability*", Clin. Phys. Physiol. Meas. 1989; 10:27-31. The contents of the aforementioned document are incorporated herein by reference. In a non-limiting example, the PSD may be sampled at 128 frequencies between 0 and the Nyquist frequency of 2 Hz to resolve the majority of the resonances. FIG. 6 of the drawings shows and example of power spectral density (PSD) estimates for a typical epoch (20 min) with the LF, MF and HF frequency bands indicated.

Optionally the power spectral density (PSD) spectrum may be integrated over low frequency (LF, 30-150 mHz), medium (movement) frequency (MF, 150-500 mHz) and high frequency (500 to 1000 mHz) bands to obtain three (3) instantaneous components of fHRV. In particular, at each (1 s) time interval j, the LF, MF and HF power spectral density (PSD) bands can be summed to give instantaneous band estimates $fHRV_{LF}(j)$, $fHRV_{MF}(j)$ and $fHRV_{HF}(j)$. Relative band energies (in units of $bpm^2$) may also be calculated by summing the spectrum over each frequency band. In specific implementations, this result can be scaled by the variance of the fHRV to calculate absolute band energies. The square root of these energies allows obtaining $fHRV_{LF}$, $fHRV_{MF}$ and $fHRV_{HF}$ in more interpretable units of bpm (beats per minute).

Once the processing of step 500 is complete, the derived fetal heart rate variability (fHRV) measurements (or the band estimates $fHRV_{LF}(j)$, $fHRV_{MF}(j)$ and $fHRV_{HF}(j)$) are released.

Optionally, following step 500 the process may proceed to step 502. At step 502, an indication of the background state of the heart rate variability, also referred to as quiescent variability $fHRV_Q$, and/or an indication of the perturbed state of the heart rate variability, also referred to as peak variability $fHRV_P$ may be derived.

Generally stated, the quiescent variability reflects the resting state of the fetal brain activity. That is, quiescent variability represents the functional interplay of sympathetic and parasympathetic systems absent external disturbing influences, such as for example contractions or fetal movement. The level of quiescent variability fHRV$_Q$ in itself may be helpful to distinguish healthy and unhealthy fetal brain states. Very low quiescent values represent a depressed level of resting function. Variability of fetal heart rate fluctuates naturally and in response to perturbing influences. Peak variability reflects the upper levels of variability achieved in response to a perturbing factor such as a contraction or fetal movement.

In a specific implementation, fHRV$_{P,Q}$ may be derived by computing a probability distribution function (pdf) using any suitable conventional method over an epoch of T$_e$ 510. In a specific implementation, the epoch T$_e$ used has duration of 20 min and a probability distribution function (pdf) is computed for each of the LF, MF and HF frequency bands. In a non-limiting example, for each band (LF, MF and HF) the quiescent component fHRV$_Q$ can be computed from the 5$^{th}$ percentile of the pdfs and the peak component fHRV$_P$ can from the 95$^{th}$ percentiles of the pdfs. FIG. 7 of the drawings shows an examples of probability distribution functions (pdfs) for LF, MF and HF frequency bands where the fHRV$_{P,Q}$ components correspond to the 5$^{th}$ percentile and 95$^{th}$ percentiles of these distributions.

In implementations which include optional step 502, the quiescent and peak variability components fHRV$_{Q,P}$ may also be released.

Returning now to FIG. 3, at step 304, a system identification (SI) process is applied to derive a system response for modeling the relationship between the uterine activity, as conveyed by signal 310, and the fetal heart rate variability, as conveyed by the fetal heart rate variability measurements.

In accordance with a specific example, the relationship between uterine activity and fetal heart rate variability may be modeled at least in part as a system having the (pre-processed) uterine activity signal 310 as an input and the fetal heart rate variability measurements (over the entire frequency spectrum or in one or more frequency bands) as an output. In some embodiment, multiple system responses associated with respective frequency bands may be derived for modeling the relationship between the uterine activity and the fetal heart rate variability in one or more frequency bands.

Figure 4A:
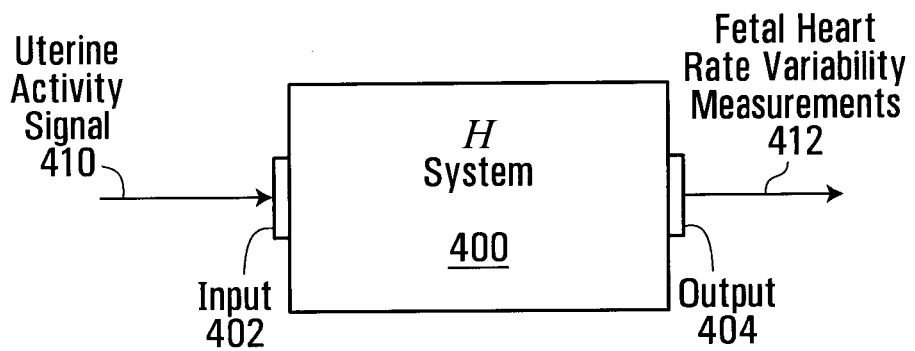
FIGS. 4A and 4B show conceptual block diagrams of systems associated with respective system responses modeling relationships between uterine activity and fetal heart rate variability in accordance with specific examples of implementation of the present invention.

FIG. 4A graphically illustrates the above concept of modeling the relationship between uterine activity and fetal heart rate variability as a system according to a first example. As shown in FIG. 4A, a system 400 to be modeled has a system response H, which when it is applied to a uterine activity signal 410 received at an input 402 yields fetal heart rate variability measurements 412 at an output 404. As will be appreciated, the system response H models the dynamics between the input uterine activity signal 410 and the out fetal heart rate variability measurements 412. As the input and output of the system 400 are known, the system response H can be derived using any suitable system identification approach.

The system response H derived by the system identification process may be associated with one or more system response parameters conveying characteristics of the system response. For example, in a case where the system response is modeled linearly as an impulse response function, the system response parameter may include, for example but not limited to:

a delay parameter conveying a delay between a rise in uterine pressure conveyed by the uterine activity signal and a change in the fetal heart rate variability;

a gain parameter conveying an amount or magnitude of change in the fetal heart rate variability following the rise in uterine pressure. In specific implementation, the gain parameter may be derived by computing the area under the IRF curve (for example by taking the sum of the IRF coefficients h(i)xTs where Ts is the sampling period);

a duration parameter conveying a time delay for the fetal heart rate variability to return to its original state following a rise in uterine pressure.

A specific example of a system identification approach wherein the system response H is modeled linearly as an impulse response function will be described later on in the present document. The person skilled in the art will appreciate, in light of the present description, that the system response H may be modeled linearly or non-linearly using any suitable function in alternate embodiments. In a specific non-limiting example, the system response H may be modeled non-linearly as a Volterra series.

Figure 4B:
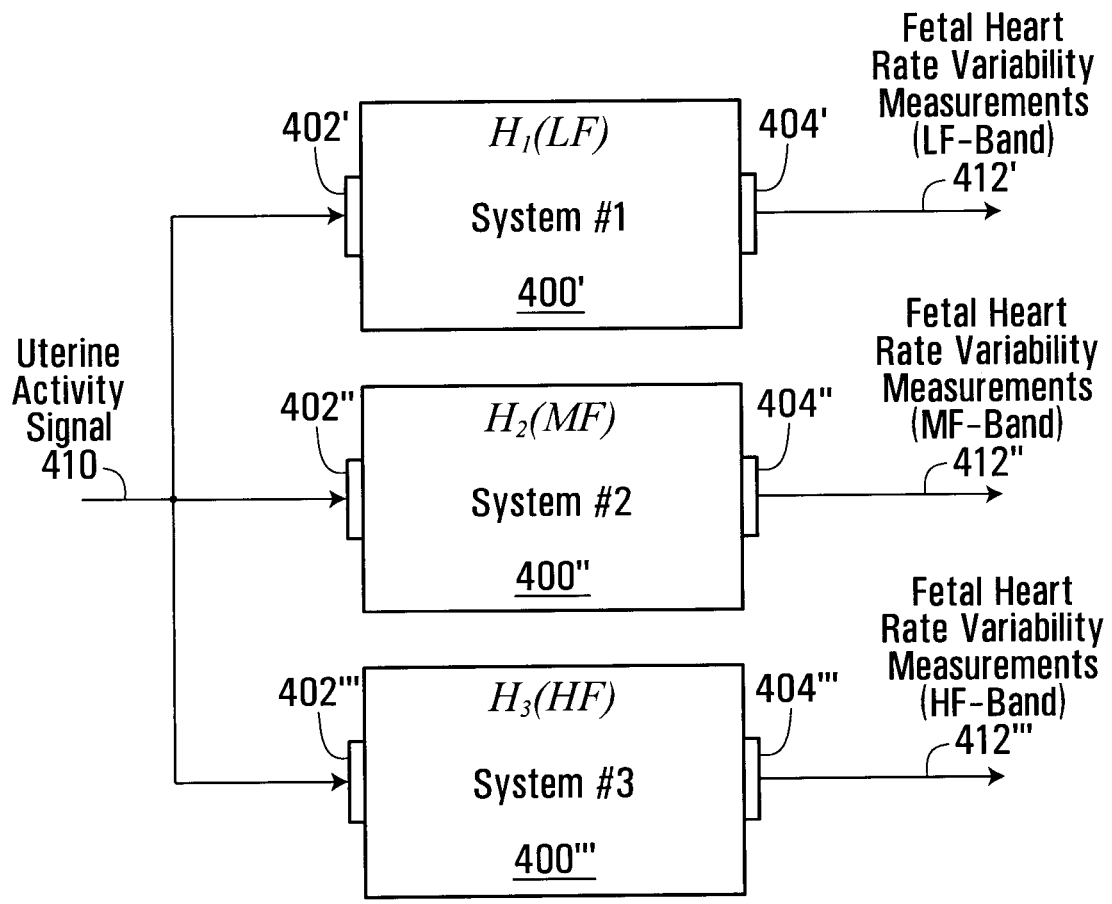

FIG. 4B illustrates the above concept of modeling the relationship between uterine activity and fetal heart rate variability as a set of systems according to a second example. In this second example, the relationship between uterine activity and fetal heart rate variability are modeled separately for different frequency bands. In this example, the fetal heart rate variability measurements 412 are comprised of measurements associated with three frequency bands namely:

fetal heart rate variability measurements 412' associated with a low frequency (LF) band—(30 to 150 mHz);

fetal heart rate variability measurements 412" associated with a medium or movement frequency (MF) band—(150 to 500 mHz); and fetal heart rate variability measurements 412''' associated with a high frequency (HF) band—(500 to 1000 mHz).

As shown in FIG. 4B, the set of systems to be modeled includes systems 400' 400" 400''' each of which is associated with a respective frequency band of the fetal heart rate variability. The systems 400' 400" 400''', which are analogous to system 400 shown in FIG. 2, are associated with respective system responses H$_1$(LF), H$_2$(MF) and H$_3$(HF). The systems 400' 400" 400''' include respective inputs 402' 402" and 402''', analogous to input 402 shown in FIG. 2, as well as respective outputs 404' 404" and 404''', analogous to output 404 shown in FIG. 2. When the system response H$_1$(LF) of system 400' is applied to the uterine activity signal 410 received at input 402', the fetal heart rate variability measurements 412' in the LF band are obtained at the output 404'. Similarly, when the system response H$_2$(MF) of system 400" is applied to the uterine activity signal 410 received at input 402", the fetal heart rate variability measurements 412" in the MF band are obtained at the output 404". Similarly still, when the system response H$_3$(HF) of system 400''' is applied to the uterine activity signal 410 received at input 402''', the fetal heart rate variability measurements 412''' in the HF band are obtained at the output 404'''.

As will be appreciated, the system responses H$_1$(LF), H$_2$(MF) and H$_3$(HF) model the respective dynamics between the input uterine activity signal 410 and the output fetal heart rate variability measurements 412' 412" and 412''' in the different frequency bands. As the input and outputs of the systems 400' 400" and 400''' are known, the system responses the system responses H$_1$(LF), H$_2$(MF) and H$_3$(HF) can be derived using any suitable system identification approach in a manner similar to the system response H.

Returning to FIG. 3, once the modeled the relationship between the uterine activity and the fetal heart rate variability has been derived and step 304 is completed, the process proceeds to step 208, shown in FIG. 2.

Processing the Modeled Relationship to Derive Fetal Well-Being Information

As described above with reference to FIG. 2, at step 208, fetal well-being information is derived by processing the modeled relationship between uterine activity and fetal heart rate variability resulting from step 206. The fetal well-being information may be derived based on the modeled relationship alone or by considering the modeled relationship as one factor amongst a set of labour progression factors. Persons skilled in the art will readily appreciate how factors other than the ones described here may also be taken into account when deriving fetal well-being information.

FIG. 8 is a flow diagram showing in greater detail a manner in which step 208 of the process depicted in FIG. 2 may be implemented for deriving fetal well-being information using the modeled relationship between the uterine activity and the fetal heart rate variability derived at step 206 in accordance with a specific example of implementation of the present invention.

At step 800, a comparison between the modeled relationship between the uterine activity and the fetal heart rate variability associated with the baby being monitored is performed against reference relationships stored in a database 804 in order to derive ranking information conveying a degree to which the baby being monitored is likely to be having an adverse response to hypoxic conditions.

The comparison may be performed using any suitable classification approach, including, but not limited to, decision trees, neural networks and support vector machines.

The ranking data element is derived based on such comparison to convey a degree to which the modeled relationship derived at step 206 more closely resembles reference relationships associated with deliveries in which metabolic acidemia developed and reference relationships is associated with deliveries that were normal. Any suitable method for deriving a ranking data element conveying this information may be used and the specific manner in which the ranking is derived may vary between implementations. In this context, the database 804 may store a set of reference relationships between uterine activity and fetal heart rate variability where:

one of the reference relationships is associated with a low likelihood of having an adverse response to hypoxic conditions; and another one of the reference relationships is associated with a high likelihood of having an adverse response to hypoxic conditions.

The relationships in the database 804 may be derived by applying a process similar to that applied at step 206 to fetal heart rate signals and uterine activity signals associated with deliveries in which metabolic acidemia developed (to derive reference relationships associated with high likelihoods of having adverse response to hypoxic conditions) and with deliveries that were normal (to derive reference relationships associated with low likelihoods of having adverse responses to hypoxic conditions). It is noted that more than one reference relationship associated with a low likelihood of having an adverse response to hypoxic conditions and more than one reference relationship associated with a high likelihood of having an adverse response to hypoxic conditions may be stored in the database 804.

In a specific example of implementation, the reference relationships stored in the database 804 are associated with respective model parameters in order to simplify comparing these reference relationships with the modeled relationships derived in step 206. The use of model parameters that convey statistically significant differences between normal (N) deliveries and those deliveries that developed metabolic acidemia (M) will be preferably used in practical implementations.

One of the parameters that experimental data has revealed to be statistically significant is the delay parameter. As such, in a specific example of implementation, the reference relationships stored in the database 804 are associated with respective delay parameters and the ranking data element is derived at least in part by comparing the delay parameter associated with the modeled relationships derived in step 206 and the delay parameters associated with the reference relationships.

In particular, generally it was found that the impulse response function (IRF) delay had statistically significant differences between normal (N) deliveries and those deliveries that developed metabolic acidemia (M). To support this, experimental data was obtained using clinically measured intrapartum cardiotocography (CTG) data (fetal heart rate signals and uterine activity signals) from singleton, term pregnancies having no known congenital malformations, with >=3 hours of tracing just prior to delivery. 89 of the cases were normal (N) while 142 had developed metabolic acidemia (M) based on outcome information (blood gases and neurological assessment). The fHRV measurements were estimated using an autoregressive model of the fetal heart rate signal to estimate the power spectral density (PSD). The autoregressive model used for the experiments was of the type described in as described in P. A. Warrick and E. F. Hamilton, "Fetal heart-rate variability response to uterine contractions during labour and delivery," in Computing in Cardiology, vol. 39, 2012, pp. 417-420. The PSD was integrated over low frequency (LF, 30-150 mHz) and movement frequency (MF, 150-500 mHz) and high frequency (HF, 500-1000 mHz) bands to obtain three instantaneous components of fHRV. System identification was performed over 20 minute epochs using the uterine activity signal (uterine pressure (UP)) as an input and one of the fHRV components (LF, MF or HF) as an output. A linear system identification approach, linear regression, was used to estimate the system models. Because of uterine pressure periodicity, there was no unique system model; searching for a "best" model was performed by shifting the output signal with respect to the input to find an impulse response function (IRF) beginning with a first coefficient near 0. The associated shift represented the delay of the output response relative to the input onset. A negative delay indicates that the response preceded the input (due to UP measurement delay).

FIG. 11 shows graphs conveying delays of the impulse response function (IRF) from system identification using uterine pressure as an input and three bands of fetal heart rate variability (fHRV) as outputs: (a) low frequency 1104 (LF) (b) movement frequency (MF) 1102 and (c) high frequency (HF) 1100. The horizontal axis is the time in minutes with respect to the time of delivery (occurring at time "0" on each of the horizontal axis) and the vertical axis is the delay in seconds. The means of the delay are plotted with bars indicating standard error and the asterisks (*) indicate statistically significant differences between normal deliveries (black circles) and metabolic acidotic (blue triangles) deliveries at that epoch (p<0.05, in the Kolmogorov-Smirnov distribution test).

Referring to FIG. 11, it can be seen that the impulse response function (IRF) delay, which can be considered as one of the parameters of the IRF, had statistically significant differences between normal (N) deliveries and those deliveries that developed metabolic acidemia (M) in each of the three frequency bands. The HF band, shown in graph 1100, had the most epochs (3) with significant differences (denoted with a * above the graph). The differences were more pronounced with M deliveries having longer delays, at 120 min (HF band) and 90 min (LF band, shown in graph 1104, and MF band, shown in graph 1102) preceding delivery.

Once the processing at step 800 is completed and ranking information conveying a degree to which the baby being monitored is likely to be having an adverse response to hypoxic conditions has been derived, the process proceeds to step 802.

At step 802, fetal well-being information is derived at least in part based on the ranking information derived at step 800. Optionally, additional factors 810 and metrics may also be taken into account to derive the fetal well-being information. Such additional factors may include, for example but not limited to:

the quiescent component of fetal heart rate variability $fHRV_Q$ derived at step 510 (shown in FIG. 5);
other metrics derived from the fetal heart rate signal and the uterine activity signal;
cervical dilations measurements;
level of descent measurements;
maternal weight, age and height;
maternal blood pressure; and
fetal oxygen saturation.

The fetal well-being information may be conveyed in different format and may depend in part on particular preferences of the clinical staff. For example, the fetal well-being information may simply convey the ranking data element derived at step 800 within a range of possible ranking data elements. Alternatively, the fetal well-being information may convey the derived ranking data element relative to reference ranges of ranking data elements to convey more explicitly a perceived level of risk that the baby of developing injury.

Alternatively still, the fetal well-being information may convey more generally a level of risk associated with the delivery that takes into account the derived ranking data element conveying a degree to which the baby being monitored is likely to be having an adverse response to hypoxic conditions as well as other factors of the type described above.

Once the processing at step 802 is completed and the fetal well-being information has been derived, the process proceeds to step 210, described above with reference to FIG. 2. Factor Based on the Quiescent Component of Fetal Heart Rate Variability ($fHRV_Q$)

As indicated above, many factors can be used to fetal well-being during labour. In the present section, the use of a factor based in part on a quiescent component of fetal heart rate variability $fHRV_Q$ is described. This factor may be used alone or in combination with other factors, including the modeled relationship between uterine activity and fetal heart rate variability described earlier in the present document, in order to derive information conveying fetal well-being.

It has been found that while modeling a relationship between uterine activity and fetal heart rate variability (for example using system identification) may be useful in characterizing the variability response relative to uterine pressure changes, the quiescent component of fetal heart rate variability $fHRV_Q$ reflects minimal unperturbed brain influence on heart rate variability. The use of these two factors in combination allows for complementary information, including perturbed (by contractions) and unperturbed fetal heart rate variability characteristics, to be taken into account when assessing fetal well-being.

Optionally, peak variability $fHRV_P$ may also be considered in combination with the above two factors when assessing fetal well-being. It is noted that as the peak variability component of fetal heart rate variability $fHRV_P$ reflects the upper levels of variability achieved in response to a perturbing factor such as a contraction or fetal movement, the information provided by this parameter overlaps to some extent, and has been found to be less informative than, the information conveyed by the modeled relationship between uterine activity and fetal heart rate variability.

FIG. 15 shows a process that may be implemented by a system of the type depicted in FIG. 1 of the drawings. With regard to this specific aspect, the processor 106 is programmed to implement a process using the quiescent component of fetal heart rate variability $fHRV_Q$, in order to derive information conveying fetal well-being. An example of such a process will now be described with reference to FIG. 15 of the drawings.

At step 1500, a fetal heart rate signal obtained from the fetal heart rate sensor 110 (shown in FIG. 1) is received. In a specific example of implementation, the fetal heart rate signal received at step 1500 conveys samples of the heart rate signal. Following receipt of the signal at step 200 the process proceeds to step 1504.

At step 1504, the fetal heart rate signal is processed by to derive fetal well-being information. In the specific example of implementation depicted, the processing of the fetal heart rate signal is shown as comprising two steps, namely: a) step 1506, where the fetal heart rate signal is processed to derive a quiescent variability measurement conveying a background state of fetal heart rate variability; and then b) step 1508, where fetal well-being information is derived at least in part by performing a comparison between the quiescent variability measurement resulting from step 1506 and reference quiescent variability measurements. The specific manner in which steps 1506 and 1508 may be put into practice in practical implementations will be described later on in the present document with reference to FIGS. 16 and 17 respectively. Following step 1504, the process proceeds to step 1510.

At step 1510, a signal for causing the fetal well-being information derived by step 1504 to be conveyed by output unit 114 (shown in FIG. 1) is released at output 108 (also shown in FIG. 1). In a specific example in which the output unit 114 includes a display device, the signal released causes information to be conveyed on the display device to assist clinicians in identifying whether the baby being monitored is exhibiting an adverse response to hypoxic conditions. The specific manner in which such information may be conveyed may vary from one implementation to the other and may depend on many factors including for example preferences of the clinical staff and/or medical establishments.

FIG. 16 is a flow diagram showing in greater detail a manner in which step 1506 of the process depicted in FIG. 15 may be implemented for deriving a quiescent variability measurement conveying a background state of fetal heart rate variability.

At step 1600, the fetal heart rate signal received at step 1500 shown in FIG. 15 is pre-processed in order to segment the fetal heart rate into time segments or epochs and to clean the fetal heart rate by removing undesirable artifacts including noise. The preprocessing of the fetal heart rate signal at step 1600 is the same as the preprocessing of the fetal heart rate signal described with reference to step 300 (shown in FIG. 3) and therefore will not be described further here. Once the fetal heart rate signal has been preprocessed, the process proceeds to step 1602.

At step 1602, which is analogous to step 500 shown in FIG. 5, the (pre-processed) heart rate signal is processed to derive fetal heart rate variability (fHRV) measurements. In the example shown the (pre-processed) heart rate signal is processed to estimate the power spectral density (PSD). Power spectral densities (PSD) of the autoregressive models can be computed using any suitable approach. Optionally the power spectral density (PSD) spectrum may be integrated over low frequency (LF, 30-150 mHz), medium (movement) frequency (MF, 150-500 mHz) and high frequency (500 to 1000 mHz) bands to obtain three (3) instantaneous components of fHRV. In particular, at each (is) time interval j, the LF, MF and HF power spectral density (PSD) bands can be summed to give instantaneous band estimates $fHRV_{LF}$ (j), $fHRV_{MF}$ (j) and $fHRV_{HF}$ (j). Relative band energies (in units of $bpm^2$) may also be calculated by summing the spectrum over each frequency band. In specific implementations, this result can be scaled by the variance of the fHRV to calculate absolute band energies. The square root of these energies allows obtaining $fHRV_{LF}$, $fHRV_{MF}$ and $fHRV_{HF}$ in more interpretable units of bpm (beats per minute). Step 1602 may be implemented in a manner similar to that described with reference to step 500 shown in FIG. 5 and therefore will not be described in further detail here.

Once the processing of step 1602 is complete the process proceeds to step 1604.

At step 1604, data conveying the background state of the heart rate variability, also referred to as quiescent variability $fHRV_Q$ is derived. Optionally data conveying the perturbed state of the heart rate variability, also referred to as peak variability $fHRV_P$ is also derived. Step 1602 may be implemented in a manner similar to that described with reference to step 502 shown in FIG. 5 and therefore will not be described in further detail here.

Following step 1604, the quiescent variability component $fHRV_Q$, and optionally the peak variability component $fHRV_P$ are released.

Once the quiescent variability component $fHRV_Q$, and optionally the peak variability component $fHRV_P$, have been derived and step 1506 is completed, the process proceeds to step 1508, shown in FIG. 15.

As described above with reference to FIG. 15, at step 1508, fetal well-being information is derived by processing the quiescent variability component $fHRV_Q$ resulting from step 1506. The fetal well-being information may be derived based on the quiescent variability component $fHRV_Q$ alone or by considering the quiescent variability component $fHRV_Q$ as one factor amongst a set of labour progression factors. Persons skilled in the art will readily appreciate how factors other than the ones described here may also be taken into account when deriving fetal well-being information.

FIG. 17 is a flow diagram showing in greater detail a manner in which step 1508 of the process depicted in FIG. 15 may be implemented for deriving fetal well-being information using the quiescent variability component $fHRV_Q$ derived at step 1506 in accordance with a specific example of implementation of the present invention.

At step 1700, a comparison between the derived the quiescent variability component $fHRV_Q$ associated with the baby being monitored is performed against reference quiescent variability components $fHRV_Q$ stored in a database 1704 in order to derive ranking information conveying a degree to which the baby being monitored is likely to be having an adverse response to hypoxic conditions. The result of the comparison may convey a degree to which the quiescent variability component $fHRV_Q$ derived at step 1506 more closely resembles reference quiescent variability component $fHRV_Q$ associated with deliveries in which metabolic acidemia developed and reference quiescent variability component $fHRV_Q$ is associated with deliveries that were normal. The comparison may be performed using any suitable classification approach, including, but not limited to, decision trees, neural networks and support vector machines in order to obtain a ranking of the derived quiescent variability component $fHRV_Q$.

In this context, the database 1704 may store a set of reference quiescent variability component $fHRV_Q$ where:
  at least one of the reference quiescent variability component $fHRV_Q$ is associated with a high likelihood of having adverse response to hypoxic conditions;
  at least another one of the reference quiescent variability component $fHRV_Q$ is associated with a low likelihood of having adverse responses to hypoxic conditions.

The reference quiescent variability component $fHRV_Q$ in the database 804 may be derived by applying a process similar to that applied at step 1506 to fetal heart rate signals associated with deliveries in which metabolic acidemia developed (to derive reference quiescent variability component $fHRV_Q$ associated with high likelihoods of having adverse response to hypoxic conditions) and with deliveries that were normal (to derive reference relationships associated with low likelihoods of having adverse responses to hypoxic conditions). It is noted that more than one reference quiescent variability component $fHRV_Q$ associated with a low likelihood of having an adverse response to hypoxic conditions and more than one reference quiescent variability component $fHRV_Q$ associated with a high likelihood of having an adverse response to hypoxic conditions may be stored in the database 1704.

Once the processing at step 1700 is completed and ranking information conveying a degree to which the baby being monitored is likely to be having an adverse response to hypoxic conditions has been derived, the process proceeds to step 1702.

At step 1702, fetal well-being information may be derived at least in part based on the ranking information derived at step 1700. Optionally, additional factors 1710 may also be taken into account to derive the fetal well-being information. Such additional factors 1710 may include, for example but not limited to:
  modeled relationship between uterine activity and fetal heart rate variability described earlier in the present document;
  the peak component of fetal heart rate variability $fHRV_P$;
  other metrics derived from the fetal heart rate signal and the uterine activity signal;
  cervical dilations measurements;
  level of descent measurements;
  maternal weight, age and height;
  maternal blood pressure; and
  fetal oxygen saturation.

The fetal well-being information may be conveyed in different format and may depend in part on particular preferences of the clinical staff. For example, the fetal well-being information may simply convey the ranking data element derived at step 1700 within a range of possible ranking data elements. Alternatively, the fetal well-being information may convey the derived ranking data element relative to reference ranges of ranking data elements to convey more explicitly a perceived level of risk that the baby of developing injury.

Once the processing at step 1508 is completed and the fetal well-being information has been derived, the process proceeds to step 1510, described above.

Example of System Identification Approach

A specific example of a system identification approach that may be implementation at step 304 to model the system response H of a system as an impulse response function will now be described.

In the specific example described below, the relationship between fetal heart rate variably and uterine activity is modeled using a linear system identification approach, as shown schematically in FIG. 12. Step 304 receives as inputs the (pre-processed) uterine activity signal 310 (segmented into 20 min epoch) and fetal heart beat variability measurements. In the specific example presented below for the purpose of illustration, the (pre-processed) uterine activity signal 310 will be denoted "u" and the fetal heart beat variability measurements will be denoted "f" and will includes power spectral densities (PSDs) summed into three bands LF, MF and HF, denoted $fHRV_{LF}$, $fHRV_{MF}$ an $fHRV_{HF}$. Next, using linear regression methods, the impulse response function (IRF) $\hat{h}$ is estimated and the best values i for the IRF delay "d" are determined. Finally, the models are validated by surrogate testing.

In the linear model, let the input uterine activity and output fetal heart rate variability (fHRV) at time sample k (k=1 ... N) be denoted by u(k) and f (k), respectively. The linear response f (k) of a discrete-time system to an arbitrary input signal u(k) is given by a convolution sum, which can be expressed mathematically as:

$$f(k) = \sum_{i=d}^{d+M-1} (h_i \Delta t) u(k-i) = h * u(k)$$

where $\Delta t$ is the sampling period, and h is the impulse response function (IRF) beginning at delay sample d, and of length M. u(k) is the length-M vector of input samples $[u_{k-d-M+1} \ldots u_{k-d-1} \, u_{k-d}]$ used to compute f (k) at sample k. For causal (physically realizable) systems, d≥0, but under certain conditions, such as input measurement delay, d may be negative. For additional explanation, the reader is invited to refer to I. W. Hunter and R. E. Kearney, "Two-sided linear filter identification," Med. Biol. Eng. Comput., vol. 21, pp. 203-209, 1983. The contents of the aforementioned documents are incorporated herein by reference.

Step 1202 shown in FIG. 12 derives a candidate impulse response function (IRF), denoted candidate h 1206 in the figure, based on the uterine activity 310 the fetal heart rate variability (fHRV) measurements. Do to so, the following mathematical relationship may be considered:

Let U be an N×M Toeplitz matrix formed from $u_n$. The least-squares estimate of h may be mathematically expressed as:

$$\hat{h} = (U^T U)^{-1} U^T f \approx \Phi_{uu}^{-1} \phi_{uf}$$

where, for N>>M, $U^T U$ and $U^T f$ may be estimated by the input autocorrelation matrix $\Phi_{uu}$ and the input-output crosscorrelation $\phi_{uf}$, respectively. An objective of the impulse response function (IRF) delay estimation is to identify the temporal extent of the IRF. This means searching for IRFs that:
1) start and end close to zero amplitude;
2) are as short as possible; and
3) are most predictive of the output.

Once step 1202 is completed and that a candidate impulse response function (IRF), denoted candidate h 1206, has been obtained, the process proceeds to step 1204.

At step 1204, which is indicated as optional in the figure, the candidate impulse response function (IRF) derived at step 1202 is validated. In particular, the step of validating is useful to ensure that the candidate impulse response function (IRF) models a relationship between the uterine activity and the fetal heart rate variability rather than effects of noise on the different signals. In a specific implementation, in order to be confident that the resulting candidate impulse response function (IRF) captures system dynamics rather than noise, impulse response functions (IRF) are also estimated on a set of surrogate FHR signals, which may for example be derived by using simulated annealing. For additional information pertaining to simulated annealing, the reader is invited to refer to T. Schreiber and A. Schmitz, "Surrogate time series," Physica D: Nonlinear Phenomena, vol. 142, no. 3-4, pp. 346-382, August 2000. The contents of the aforementioned document are incorporated herein by reference.

Generally speaking in simulated annealing, samples are randomly swapped and a cost function E determines whether the interchange is accepted. In a specific example, E was set to the sum of squared differences between the auto-correlation functions of the original fetal heart rate signal (FHR) and the surrogates. If the surrogate FHR more closely matched the original ($\Delta E<0$), the swap was accepted. Otherwise it was accepted with probability $p=e^{-\Delta E/T}$. The samples were first fully randomized and T was set to a high value. In subsequent iterations, T was gradually lowered so that p reduced towards zero until E converged.

The gap locations in the surrogates are fixed to those in the original; gaps are excluded from swapping but included in the auto-correlation function on the assumption that they had equal influence on the cost function. In order to allow more variability in the surrogates, rather than fixing the gap data to a constant, the gap values may be randomized over the range of the signal just before and after the gap. To speed up calculations, the length of the autocorrelation function may be limited to a fixed number of sample, for example to 256 samples (a conservative upper bound on the first zero crossing, as determined by preliminary experimentation) and a suitable approach may be used to re-calculate only those terms of the auto-correlation that were changed by the swap. For additional information, the reader may wish to refer to I. W. Hunter and R. E. Kearney, "Generation of random sequences with jointly specified probability density and autocorrelation functions," Biological Cybernetics, vol. 47, no. 2, pp. 141-146, June 1983. The contents of the aforementioned document are incorporated herein by reference.

The generation of surrogates FHR signal may be limited to a small number (e.g. 3) and the derived candidate impulse response function (IRF) 1206 may be accepted if the fidelity of the candidate impulse response function (IRF) 1206 with the original FHR is greater than all of the impulse response function (IRF) generated from the surrogate data. This gives a confidence level of 75% that a candidate impulse response function (IRF) 1206 capturing spurious dynamics would be rejected.

Once the validation step 1204 have been completed, if the candidate impulse response function (IRF) 1206 is accepted, the impulse response function (IRF) modeling a relationship between uterine activity and fetal heart rate variability is released.

FIG. 13 includes graphs showing a preprocessed uterine activity signal 1300, fetal heart rate variability measurements in the movement frequency band (fHRV$_{MF}$) (shown using a thin line in 1302), model-predicted fetal heart rate variability measurements (shown in a thicker lines in 1302) and an impulse response function (IRF) 1304. The model parameters for the impulse response function (IRF) 1304 are:

delay: d=−16 s
gain: G=0.028 bpm/mmHg.
Variance accounted for: VAF=62.8%.

Specific Physical Implementation

Those skilled in the art should appreciate that in some embodiments of the invention, all or part of the functionality for monitoring a baby in-utero during labor previously described herein, may be implemented as pre-programmed hardware or firmware elements (e.g., application specific integrated circuits (ASICs), electrically erasable programmable read-only memories (EEPROMs), etc.), or other related components.

In other embodiments of the invention, all or part of the functionality previously described herein for monitoring a baby in-utero during labor may be implemented as a computer program product including instructions that, when executed, cause a programmable system including at least one programmable processor to perform operations. In practical implementations, the program product could be stored on a medium which is fixed (non-transitory), tangible and readable directly by the programmable system, (e.g., removable diskette, CD-ROM, ROM, PROM, EPROM, flash memory or fixed disk), or the instructions could be stored remotely but be transmittable to the programmable system via a modem or other interface device (e.g., a communications adapter) connected to a network over a transmission medium. The transmission medium may be either a wired medium (e.g., optical or analog communications lines) or a medium implemented using wireless techniques (e.g., microwave, infrared or other transmission schemes).

An apparatus for monitoring a baby in-utero implementing the functionality described above may be configured as a computing unit 900 of the type depicted in FIG. 9, including a processing unit 902 and a memory 904 connected by a communication bus 908. The memory 904 includes data 910 and program instructions 906. The processing unit 902 processes the data 910 and the program instructions 906 in order to implement the functional blocks described in the specification and depicted in the drawings. The computing unit 900 may also comprise a number of interfaces 912 914 916 for receiving or sending data elements to external devices. For example, interface 912 is used for receiving data streams indicative of a fetal heart rate signal and interface 914 is used for receiving a signal from the uterine activity sensor 111. Interface 916 is for releasing a signal causing a display unit to display the user interface generated by the program instructions 906. The processing unit 902 is operative for processing the signals to derive information conveying an insight into the well-being of a fetus during labor progression. The information is then released at output inter 906 so that it may be conveyed to a health care professional, for example by displaying information on a display device.

It will be appreciated that a system for monitoring a baby in-utero during labor implementing the functionality described above may also be of a distributed nature where information data elements associated to an obstetrics patient are collected at one location and transmitted over a network to a server unit implementing the method as described above. The server unit may then transmit a signal for causing an output unit to convey information to the clinical staff using a display device, such as a display screen or a printing device for example. The display device may be located in the same location where the information data elements are being obtained or in the same location as the server unit or in yet another location.

FIG. 10 illustrates a network-based client-server system 1000 for monitoring a baby in-utero during labor. The client-server system 1000 includes a plurality of client systems 1012 1014 1016 1018 connected to a server system 1010 through network 1020. The communication links 1050 between the client systems 1012 1014 1016 1018 and the server system 1010 can be metallic conductors, optical fibers or wireless, without departing from the spirit of the invention. The network 1020 may be any suitable network including but not limited to a global public network such as the Intranet, a private network and a wireless network. The server 1010 may be adapted to process signals originating from multiple sensors 1026 1028 concurrently using suitable methods known in the computer related arts. The server 1010 executes program code 1060 implements methods described in the present document for monitoring a baby in-utero during labor.

Although the present invention has been described with reference to certain preferred embodiments thereof, variations and refinements are possible and will become apparent to the person skilled in art in light of the present description. Therefore, the scope of the invention should be limited only by the appended claims and their equivalents.

The invention claimed is:

1. A method for monitoring a baby in-utero during labor, said method being implemented by a system including at least one programmable processor and comprising:
   a. receiving a fetal heart rate signal from a fetal heart rate sensor;
   b. receiving a uterine activity signal from a uterine activity sensor;
   c. processing the fetal heart rate signal and the uterine activity signal to derive fetal well-being information at least in part by:
      i. processing the fetal heart rate signal and the uterine activity signal to model a relationship between uterine activity and fetal heart rate variability, the modeled relationship including relationship modeling components associated with respective frequency bands in a set of at least two distinct frequency bands;
      i. deriving the fetal well-being information by processing the modeled relationship between the uterine activity and the fetal heart rate variability at least in part based on a reference relationship, the reference relationship including reference relationship components associated with respective ones of the at least two distinct frequency bands;
   d. releasing a signal for causing the fetal well-being information to be displayed on a display device to assist clinicians in identifying whether the baby being monitored is exhibiting an adverse response to hypoxic conditions.

2. A method as defined in claim 1, wherein processing the fetal heart rate signal and the uterine activity signal to model the relationship between uterine activity and fetal heart rate variability includes processing the fetal heart rate signal at least in part to derive variability measurements.

3. A method as defined in claim 2, wherein the relationship between uterine activity and fetal heart rate variability is modeled at least in part as a set of systems having the uterine activity signal as an input and the variability measurements as an output, the systems in the set of system being associated with respective ones of the at least two distinct frequency bands.

4. A method as defined in claim 3, wherein the systems are associated with respective system responses derived at least in part by using a system identification approach.

5. A method as defined in claim 4, wherein the system responses are associated with system response parameters.

6. A method as defined in claim 5, wherein the system response parameters include at least one of:
   a. a delay parameter conveying a delay between a rise in uterine pressure conveyed by the uterine activity signal and a change in the fetal heart rate variability;
   b. a gain parameter conveying an amount of change in the fetal heart rate variability following a rise in uterine pressure;
   c. a duration parameter conveying a time delay for the fetal heart rate variability to return to its original state following a rise in uterine pressure.

7. A method as defined in claim 4, wherein at least one of the system responses is modeled linearly as an impulse response function.

8. A method as defined in claim 1, wherein deriving the fetal well-being information at least in part by processing the modeled relationship between the uterine activity and the fetal heart rate variability includes for at least one of the at least two distinct frequency bands:
   performing a comparison between the relationship modeling components of the modeled relationship between the uterine activity and the fetal heart rate variability associated with the at least one of the at least two distinct frequency bands with a set of reference relationships to derive ranking information conveying a degree to which the baby being monitored is likely to be having an adverse response to hypoxic conditions;
   deriving the fetal well-being information at least in part based on said ranking information.

9. A method as defined in claim 8, wherein at least one of the reference relationships is associated with deliveries in which metabolic acidemia developed.

10. A method as defined in claim 8, wherein:
    at least one of the reference relationships is associated with deliveries in which metabolic acidemia developed;
    at least another one of the reference relationships is associated with deliveries that were normal.

11. A method as defined in claim 1, wherein the at least two distinct frequency bands include a first frequency band and a second frequency band, and wherein the modeled relationship between uterine activity and fetal heart rate variability includes:
    a first relationship modeling component for modeling a relationship between the uterine activity and the fetal heart rate variability in the first frequency band;
    a second relationship modeling component for modeling a relationship between the uterine activity and the fetal heart rate variability in the second frequency band, the second frequency band being distinct from the first frequency band.

12. A method as defined in claim 11, wherein:
    the first relationship modeling component is associated with a first set of system response parameters;
    the second relationship modeling component is associated with a second set of system response parameters.

13. A computer program product for monitoring a baby in-utero during labor, the program product comprising instructions tangibly stored on one or more tangible computer readable storage media, said instructions, when executed, cause a programmable system including at least one programmable processor to implement operations comprising:
    a. receiving a fetal heart rate signal from a fetal heart rate sensor;
    b. receiving a uterine activity signal from a uterine activity sensor;
    c. processing the fetal heart rate signal and the uterine activity signal to derive fetal well-being information at least in part by:
       i. processing the fetal heart rate signal and the uterine activity signal to model a relationship between uterine activity and fetal heart rate variability, the modeled relationship including relationship modeling components associated with respective frequency bands in a set of at least two distinct frequency bands;
       ii. deriving the fetal well-being information by processing the modeled relationship between the uterine activity and the fetal heart rate variability at least in part based on a reference relationship, the reference relationship including reference relationship components associated with respective ones of the at least two distinct frequency bands;
    d. releasing a signal for causing the fetal well-being information to be displayed on a display device to assist clinicians in identifying whether the baby being monitored is exhibiting an adverse response to hypoxic conditions.

14. An apparatus for monitoring a baby in-utero during labor, said apparatus comprising:
    a. at least one input for receiving a fetal heart rate signal from a fetal heart rate sensor and a uterine activity signal from a uterine activity sensor;
    b. a processor in communication with said at least one input, said processor being programmed for processing the fetal heart rate signal and the uterine activity signal to derive fetal well-being information at least in part by:
       processing the fetal heart rate signal and the uterine activity signal to model a relationship between uterine activity and fetal heart rate variability, the modeled relationship including relationship modeling components associated with respective frequency bands in a set of at least two distinct frequency bands;
       deriving the fetal well-being information by processing the modeled relationship between the uterine activity and the fetal heart rate variability at least in part based on a reference relationship, the reference relationship including reference relationship components associated with respective ones of the at least two distinct frequency bands;
    c. an output for releasing a signal causing the fetal well-being information to be displayed on a display device to assist clinicians in identifying whether the baby being monitored is exhibiting an adverse response to hypoxic conditions.

15. An apparatus as defined in claim 14, wherein processing the fetal heart rate signal and the uterine activity signal to model the relationship between uterine activity and fetal heart rate variability includes processing the fetal heart rate signal at least in part to derive variability measurements.

16. An apparatus as defined in claim 15, wherein the relationship between uterine activity and fetal heart rate variability is modeled at least in part as a set of systems having the uterine activity signal as an input and the variability measurements as an output, the systems in the set of system being associated with respective ones of the at least two distinct frequency bands.

17. An apparatus as defined in claim 16, wherein the systems are associated with respective system responses derived at least in part by using a system identification approach.

18. An apparatus as defined in claim 17, wherein the system responses are associated with system response parameters.

19. An apparatus as defined in claim 18, wherein the system response parameters include at least one of:
   a. a delay parameter conveying a delay between a rise in uterine pressure conveyed by the uterine activity signal and a change in the fetal heart rate variability;
   b. a gain parameter conveying an amount of change in the fetal heart rate variability following a rise in uterine pressure;
   c. a duration parameter conveying a time delay for the fetal heart rate variability to return to its original state following a rise in uterine pressure.

20. An apparatus as defined in claim 17, wherein at least one of the system responses is modeled linearly as an impulse response function.

21. An apparatus as defined in claim 14, wherein deriving the fetal well-being information at least in part by processing the modeled relationship between the uterine activity and the fetal heart rate variability includes for at least one of the at least two distinct frequency bands:
   performing a comparison between the relationship modeling components of the modeled relationship between the uterine activity and the fetal heart rate variability associated with the at least one of the at least two distinct frequency bands with a set of reference relationships to derive ranking information conveying a degree to which the baby being monitored is likely to be having an adverse response to hypoxic conditions;
   deriving the fetal well-being information at least in part based on said ranking information.

22. An apparatus as defined in claim 21, wherein at least one of the reference relationships is associated with deliveries in which metabolic acidemia developed.

23. An apparatus as defined in claim 21, wherein:
   at least one of the reference relationships is associated with deliveries in which metabolic acidemia developed;
   at least another one of the reference relationships is associated with deliveries that were normal.

24. An apparatus as defined in claim 14, wherein the at least two distinct frequency bands include a first frequency band and a second frequency band, and wherein the modeled relationship between uterine activity and fetal heart rate variability includes:
   a first relationship modeling component for modeling a relationship between the uterine activity and the fetal heart rate variability in the first frequency band;
   a second relationship modeling component for modeling a relationship between the uterine activity and the fetal heart rate variability in the second frequency band, the second frequency band being distinct from the first frequency band.

25. An apparatus as defined in claim 24, wherein:
   the first relationship modeling component is associated with a first set of system response parameters;
   the second relationship modeling component is associated with a second set of system response parameters.

26. A system for monitoring a baby in-utero during labor, said system comprising:
   a. a fetal heart rate sensor for generating a fetal heart rate signal;
   b. a uterine activity sensor for measuring uterine pressure and generating a uterine activity signal;
   c. the apparatus for monitoring a baby in-utero during labor defined in claim 14 in communication with said fetal heart rate sensor and said uterine activity sensor;
   d. a display device in communication with said apparatus.

* * * * *